United States Patent
Cohen et al.

(10) Patent No.: US 9,474,744 B2
(45) Date of Patent: Oct. 25, 2016

(54) BETA-LACTAM COMPOUNDS FOR TREATING DIABETES

(71) Applicant: STEM CELL MEDICINE LTD., Jerusalem (IL)

(72) Inventors: Irun R. Cohen, Rehovot (IL); Felix Mor, Kfar Saba (IL)

(73) Assignee: STEM CELL MEDICINE LTD., Jerusalem (IL)

( * ) Notice: Subject to any disclaimer, the term of this patent is extended or adjusted under 35 U.S.C. 154(b) by 0 days.

(21) Appl. No.: 14/346,219

(22) PCT Filed: Sep. 20, 2012

(86) PCT No.: PCT/IL2012/050378
§ 371 (c)(1),
(2) Date: Mar. 20, 2014

(87) PCT Pub. No.: WO2013/042121
PCT Pub. Date: Mar. 28, 2013

(65) Prior Publication Data
US 2014/0234282 A1   Aug. 21, 2014

Related U.S. Application Data

(60) Provisional application No. 61/537,105, filed on Sep. 21, 2011.

(51) Int. Cl.
| A61K 31/34 | (2006.01) |
| A61K 31/43 | (2006.01) |
| A61K 47/48 | (2006.01) |
| A61K 35/17 | (2015.01) |
| A61K 38/38 | (2006.01) |

(52) U.S. Cl.
CPC .............. *A61K 31/43* (2013.01); *A61K 35/17* (2013.01); *A61K 38/385* (2013.01); *A61K 47/48284* (2013.01)

(58) Field of Classification Search
None
See application file for complete search history.

(56) References Cited

U.S. PATENT DOCUMENTS

| 6,015,809 A * | 1/2000 | Zhu et al. ............... 514/210.03 |
| 6,130,087 A | 10/2000 | Srivastava et al. |
| 6,610,681 B1 | 8/2003 | Koppel |
| 6,627,625 B1 | 9/2003 | Koppel |
| 2004/0110290 A1 | 6/2004 | June et al. |
| 2006/0160787 A1 | 7/2006 | Dou et al. |

FOREIGN PATENT DOCUMENTS

| CN | 101524517 A | 9/2009 |
| EP | 1864995 A1 | 12/2007 |
| KR | 20070025135 A | 3/2007 |
| LV | 12403 A | 12/1999 |
| WO | 94/18164 A1 | 8/1994 |
| WO | 97/21675 A1 | 6/1997 |
| WO | 99/24613 A1 | 5/1999 |
| WO | 01/12184 A1 | 2/2001 |
| WO | 03/061605 A2 | 7/2003 |
| WO | 2005/121148 A2 | 12/2005 |
| WO | 2007/099396 A2 | 9/2007 |
| WO | WO 2010057647 A2 * | 5/2010 |
| WO | 2011/047153 A1 | 4/2011 |
| WO | 2012/103456 A2 | 8/2012 |
| ZA | 1994/00128 | 8/1994 |

OTHER PUBLICATIONS

Rolinson "Forty years of beta-lactam research", Journal of Antimicrobial Chemotherapy 41(6): 589-603, 1998.*
Brander et al., (1995) "Heterogeneous T cell responses to beta-lactam-modified self-structures are observed in penicillin-allergic individuals," J Immunol., vol. 155, pp. 2670-2678.
Cottagnoud et al., (1988) "Inhibition of HSV-1 and vaccinia virus replication by cephalosporin derivatives," Antiviral Res., vol. 10, pp. 59-70.
Mor et al., (2013) "Beta-lactam antibiotics modulate T-cell functions and gene expression via covalent binding to cellular albumin," Proc Natl Acad Sci USA, vol. 110, No. 8, pp. 2981-2986.
Spanou et al., (2006) "Involvement of drug-specific T cells in acute drug-induced interstitial nephritis," J Am Soc Nephrol, vol. 17, pp. 2919-2927.
Achiron et al., (2004) Blood transcriptional signatures of multiple sclerosis: unique gene expression of disease activity. Ann Neurol 55(3): 410-417.
Bertucci et al., (2001) Binding properties of human albumin modified by covalent binding of penicillin. Biochim Biophys Acta 1544(1-2): 386-392.
Bluestone et al., (2010) Genetics, pathogenesis and clinical interventions in type 1 diabetes. Nature 464(7293): 1293-1300.
Brundula et al., (2002) Targeting leukocyte MMPs and transmigration: minocycline as a potential therapy for multiple sclerosis. Brain 125(Pt 6): 1297-1308.
Cairo and Lucchini (1993) Molecular basis of reduced albumin gene expression in hepatoma cell lines with different growth rates. Exp Cell Res 206(2): 255-260.
Calebotta et al., (1999) Pemphigus vulgaris: benefits of tetracycline as adjuvant therapy in a series of thirteen patients. Int J Dermatol 38(3): 217-221.
Chen et al., (1994) Tumor immunogenicity determines the effect of B7 costimulation on T cell-mediated tumor immunity. J Exp Med 179(2): 523-532.

(Continued)

*Primary Examiner* — Taeyoon Kim
*Assistant Examiner* — Emily Cordas
(74) *Attorney, Agent, or Firm* — Rothwell, Figg, Ernst & Manbeck, P.C.

(57) ABSTRACT

Compositions and methods comprising ampicillin or salts and derivative thereof for the treatment of delaying the onset of type I diabetes are provided.

10 Claims, 8 Drawing Sheets

(56) References Cited

OTHER PUBLICATIONS

Choi et al., (2003) Effect of moxifloxacin on production of proinflammatory cytokines from human peripheral blood mononuclear cells. Antimicrob Agents Chemother 47(12): 3704-3707.
Christie et al., (1987) Drug-protein conjugates—XIII. The disposition of the benzylpenicilloyl hapten conjugated to albumin. Biochem Pharmacol 36(20): 3379-3385.
Cornman (1944) A selective lethal effect of penicillin on sarcoma cells growing with normal tissue in roller tube cultures. J Gen Physiol 28(2): 113-118.
de Haan et al., (1985) Three epitope-specific monoclonal antibodies against the hapten penicillin. Int Arch Allergy Appl Immunol 76(1): 42-46.
Di Marco et al., (2001) Sodium fusidate (fusidin) ameliorates the course of monophasic experimental allergic encephalomyelitis in the Lewis rat. Mult Scler 7(2): 101-104.
Elias et al., (1997) Hsp60 peptide therapy of NOD mouse diabetes induces a Th2 cytokine burst and downregulates autoimmunity to various beta-cell antigens. Diabetes 46(5): 758-764.
Garren et al., (2001) Combination of gene delivery and DNA vaccination to protect from and reverse Th1 autoimmune disease via deviation to the Th2 pathway. Immunity 15(1): 15-22.
Giuliani et al., (2005) Effective combination of minocycline and interferon-beta in a model of multiple sclerosis. J Neuroimmunol 165(1-2): 83-91.
Gollapudi et al., (2003) Molecular basis of rifampicin-induced inhibition of anti-CD95-induced apoptosis of peripheral blood T lymphocytes: the role of CD95 ligand and FLIPs. J Clin Immunol 23(1): 11-22.
Gorelik et al., (1980) Control of lung metastasis progression in mice: role of growth kinetics of 3LL Lewis lung carcinoma and host immune reactivity. J Natl Cancer Inst 65(6): 1257-1264.
Huegin et al., (1986) Suppressive effects of B-lactam-antibiotics on in vitro generation of cytotoxic T-cells. Int J Immunopharmacol 8(7): 723-9.
Ishimatsu et al., (2004) Macrolide antibiotics induce apoptosis of human peripheral lymphocytes in vitro. Int J Antimicrob Agents 24(3): 49-55.
Kadota et al., (2005) Antibiotic-induced apoptosis in human activated peripheral lymphocytes. Int J Antimicrob Agents 25(3): 216-220.
Keymeulen et al., (2010) Transient Epstein-Barr virus reactivation in CD3 monoclonal antibody-treated patients. Blood 115(6): 1145-1155.
Kloppenburg et al., (1996) The tetracycline derivative minocycline differentially affects cytokine production by monocytes and T lymphocytes. Antimicrob Agents Chemother 40(4): 934-940.
Kolbach et al., (1995) Bullous pemphigoid successfully controlled by tetracycline and nicotinamide. Br J Dermatol 133(1): 88-90.
Kong et al., (2009) A novel phosphorylated STAT3 inhibitor enhances T cell cytotoxicity against melanoma through inhibition of regulatory T cells. Cancer Immunol Immunother 58(7): 1023-1032.
Krakauer and Buckley (2003) Doxycycline is anti-inflammatory and inhibits staphylococcal exotoxin-induced cytokines and chemokines. Antimicrob Agents Chemother 47(11): 3630-3633.
Kratz (2008) Albumin as a drug carrier: design of prodrugs, drug conjugates and nanoparticles. J Control Release 132(3): 171-183.
Kuhn et al., (2004) Beta-lactams and their potential use as novel anticancer chemotherapeutics drugs. Front Biosci 9: 2605-2617.
Lewis (1944) The failure of purified penicillin to retard the growth of grafts of sarcoma in mice. Science 100(2597): 314-315.
Li et al., (2001) Immune response against 3LL Lewis lung carcinoma potentiates the therapeutic efficacy of endostatin. J Immunother 24(6): 472-481.
Liu et al., (1998) TNF is a potent anti-inflammatory cytokine in autoimmune-mediated demyelination. Nat Med 4(1): 78-83.
Masharani and Becker (2010) Teplizumab therapy for type 1 diabetes. Expert Opin Biol Ther 10(3): 459-465.
Melzer et al., (2008) A beta-lactam antibiotic dampens excitotoxic inflammatory CNS damage in a mouse model of multiple sclerosis. PLoS One 3(9): e3149, 12 pages.
Mimran et al., (2004) DNA vaccination with CD25 protects rats from adjuvant arthritis and induces an antiergotypic response. J Clin Invest 113(6): 924-932.
Mor and Cohen (1993) Shifts in the epitopes of myelin basic protein recognized by Lewis rat T cells before, during, and after the induction of experimental autoimmune encephalomyelitis. J Clin Invest 92(5): 2199-2206.
Mor et al., (1990) Clinical modeling of T cell vaccination against autoimmune diseases in rats. Selection of antigen-specific T cells using a mitogen. J Clin Invest 85(5): 1594-1598.
Mor et al., (2005) Identification of aldolase as a target antigen in Alzheimer's disease. J Immunol 175(5): 3439-3445.
Nieuwenhuis et al., (2000) Oral antibiotics as a novel therapy for arthritis: evidence for a beneficial effect of intestinal *Escherichia coli*. Arthritis Rheum 43(11): 2583-2589.
Popovic et al., (2002) Inhibition of autoimmune encephalomyelitis by a tetracycline. Ann Neurol 51(2): 215-223.
Rothstein et al., (2005) Beta-lactam antibiotics offer neuroprotection by increasing glutamate transporter expression. Nature 433(7021): 73-77.
Satoh et al., (2006) T cell gene expression profiling identifies distinct subgroups of Japanese multiple sclerosis patients. J Neuroimmunol 174(1-2): 108-118.
Seikwan et al., (2007) Synthesis of new beta-lactam analogs and evaluation of their histone deacetylase (HDAC) activity. 62b: 1459-1464.
Kosiewicz et al., (2011) Gut microbiota, immunity, and disease: a complex relationship. Frontiers in Microbiology, vol. 2, Article 180, pp. 1-11.
Kranich et al., (2011) Commensal flora and the regulation of inflammatory and autoimmune responses. Seminars in Immunology, 23(2): 139-145.
Pásztói et al., (2011) Infection and autoimmunity: Lessons of animal models. European Journal of Microbiology and Immunology (Bp) 1(3): 198-207.
Grill, M.F. and Maganti, R.K., Neurotoxic effects associated with antibiotic use: management considerations. British Journal of Clinical Pharmacology, 72:3, 381-393 (2011).

* cited by examiner

Protein View

Match to: ALBU_HUMAN Score: 114

Serum albumin precursor - Homo sapiens (Human)

Found in search of C:\Temp\mas502.tmp

Nominal mass ($M_r$): 69321; Calculated pI value: 5.92
NCBI BLAST search of ALBU_HUMAN against nr
Taxonomy: Homo sapiens
Variable modifications: Carbamidomethyl (C),Deamidated (NQ),Oxidation (M)
Cleavage by Trypsin: cuts C-term side of KR unless next residue is P
Sequence Coverage: 4%

Matched peptides shown in Bold Red

```
  1 MKWVTFISLL FLFSSAYSRG VFRRDAHKSE VAHRFKDLGE ENFKALVLIA
 51 FAQYLQQCPF EDHVKLVNEV TEFAKTCVAD ESAENCDKSL HTLFGDKLCT
101 VATLRETYGE MADCCAKQEP ERNECFLQHK DDNPNLPRLV RPEVDVMCTA
151 FHDNEETFLK KYLYEIARRH PYFYAPELLF FAKRYKAAFT ECCQAADKAA
201 CLLPKLDELR DEGKASSAKQ RLKCASLQKF GERAFKAWAV ARLSQRFPKA
251 EFAEVSKLVT DLTKVHTECC HGDLLECADD RADLAKYICE NQDSISSKLK
301 ECCEKPLLEK SHCIAEVEND EMPADLPSLA ADFVESKDVC KNYAEAKDVF
351 LGMFLYEYAR RHPDYSVVLL LRLAKTYETT LEKCCAAADP HECYAKVFDE
401 FKPLVEEPQN LIKQNCELFE QLGEYKFQNA LLVRYTKKVP QVSTPTLVEV
451 SRNLGKVGSK CCKHPEAKRM PCAEDYLSVV LNQLCVLHEK TPVSDRVTKC
501 CTESLVNRRP CFSALEVDET YVPKEFNAET FTFHADICTL SEKERQIKKQ
551 TALVELVKHK PKATKEQLKA VMDDFAAFVE KCCKADDKET CFAEEGKKLV
601 AASQAALGL
```

FIGURE 2B

1= NC
2= Cyto-hAlb-Pen 1hr
3= Cyto-hAlb-Pen 2hr
4= Cyto-hAlb-Pen 3hr
5= Cyto-Pen 3hr
6= Nucl-NC
7= Nucl-hAlb-Pen 1hr
8= Nucl-hAlb-Pen 2hr
9= Nucl-hAlb-Pen 3hr
10= Nucl Pen 3hr

BETA-LACTAM COMPOUNDS FOR TREATING DIABETES

CROSS REFERENCE TO RELATED APPLICATIONS

This application is a 35 U.S.C. §371 National Phase Entry Application from PCT/IL2012/050378, filed Sep. 20, 2012, and designating the United States, which claims the benefit of U.S. Patent Application No. 61/537,105 filed Sep. 21, 2011, which are incorporated herein in their entireties.

FIELD OF THE INVENTION

The present invention relates to compositions and methods for the treatment of diabetes. Specifically, the present invention relates to the use of the beta-lactam antibiotic ampicillin or salts and derivatives thereof in diabetes treatment.

BACKGROUND OF THE INVENTION

Type I diabetes mellitus (also known as insulin-dependent diabetes, juvenile onset diabetes) is a form of diabetes mellitus that results from autoimmune destruction of insulin-producing beta-cells of the pancreas. The subsequent lack of insulin leads to increased blood and urine glucose. The classical symptoms are polyuria (frequent urination), polydipsia (increased thirst), polyphagia (increased hunger) and weight loss.

There is currently no effective cure for type I diabetes that restores the normal function of the pancreas, and treatment of type I diabetes is mainly focused on maintaining normal levels of blood sugar or glucose. Type I diabetes is usually treated with insulin replacement therapy, for example via subcutaneous injection, along with attention to dietary management and careful monitoring of blood glucose levels using glucose meters. Other treatment options include islet cell transplantation or whole pancreas transplantation, which may restore proper glucose regulation. However, as with any organ transplantation, the transplant recipient is required to take immunosuppressive drugs that are associated with a number of adverse effects, and therefore these options are not widely used. Complications of type I diabetes may be associated with both low blood sugar and high blood sugar. Low blood sugar may lead to seizures or episodes of unconsciousness and requires emergency treatment. High blood sugar may lead to increased fatigue and can also result in long term damage to organs.

Although the exact mechanism of type I diabetes development is not completely known, it is believed that auto-reactive CD4$^+$ and CD8$^+$ T lymphocytes are the main mediators of the beta-cells destruction. Other immune cells are also thought to play a role in the development and progression of the disease, for example, T regulatory (Treg) cells and T helper (Th) cells. There is also evidence implicating involvement of dendritic cells, macrophages and B lymphocytes.

The autoimmune attack directed against the beta-cells is believed to occur several years (5 years or more) before the clinical presentation of diabetes. However, even after the diagnosis of diabetes there is still significant beta-cell function, whose further decline may be prevented or arrested by immunological interventions.

Proposed immunotherapeutic interventions in type I diabetes include both antigen specific and non-antigenic specific therapy (reviewed in Masharani et al. (2010) *Expert Opin Biol Ther,* 10(3):459-65; and Bluestone et al. (2010) *Nature,* 464(7293):1293-300).

Antigen specific therapies are aimed at controlling the autoimmune process by inducing antigen specific tolerance. The rationale is to generate antigen specific regulatory T cells that induce anergy/deletion of auto-reactive effector T cells. One of the challenges in type I diabetes is identifying the pathogenic epitopes at the initiation of the disease. After the onset of the autoimmune injury, epitope spreading makes it difficult to identify specific target antigens. The antigens that have been suggested as potential tolerogens for type I diabetes include insulin and glutamic acid decarboxylase (GAD). Thus far, this approach has not been successful.

Non-antigenic specific therapy is not directed at a specific population of pathogenic T cells. For example, broad spectrum immunosuppressive agents, such as cyclosporine, azathioprine, prednisone and anti-thymocyte globulin that deplete or inactivate pathogenic T cells, have been tested for their effect on newly diagnosed type I diabetes. Although these drugs could decrease insulin requirements, the effect was modest and, as noted above, such drugs are associated with a number of adverse effects and are therefore not recommended for long term use.

The use of anti-CD3 antibodies has also been proposed as a non-antigen specific therapy that may arrest the loss of beta-cell function in new onset type I diabetes. These antibodies are specific to the c chain of the CD3 complex, which is the major signal transduction element of the T cell receptor. Clinical studies with, for example, teplizumab and otelixizumab, which are humanized anti-CD3 monoclonal antibodies, have provided evidence of preservation of insulin production in newly diagnosed type I diabetes patients, as evidenced by sustained C-peptide levels, a known indicator of endogenous insulin production. However, the duration of the effect and long-term efficacy is still unknown, and the use of anti-CD3 antibodies may induce undesirable side effects such as the activation of latent virus infections (Keymeulen B et al., (2010) *Blood,* 115(6):1145-55).

An anti-CD20 antibody, rituximab, inhibits B cells and has been shown to provoke C-peptide responses three months after diagnosis of type 1 diabetes. But, similar to the anti-CD3 antibodies, long-term effects of this antibody are still to be evaluated.

There is therefore a medical need for more effective means of type I diabetes treatment.

Beta-lactam compounds are a group of compounds containing a beta-lactam ring, namely a cyclic amide composed of three carbon atoms and one nitrogen atom. The beta-lactam ring is part of the structure of several antibiotic families, the principal ones being the penicillins, cephalosporins, carbapenems and monobactams, which are therefore referred to as beta-lactam antibiotics. These antibiotics work by inhibiting bacterial cell wall synthesis, thereby leading to a weakened cell wall and osmotic lysis of the bacterial cell. Bacteria can, however, become resistant to beta-lactam antibiotics, for example, by producing enzymes which hydrolyze the beta-lactam moiety and render the antibiotic inactive. These enzymes are generally referred to as beta-lactamases.

It was initially thought that beta-lactam antibiotics would not be able to directly affect mammalian cells, since mammalian cells do not produce cell walls. However, theoretically, beta-lactam compounds might bind eukaryotic cellular proteins and affect their functions. Indeed, screening of various compounds in models of amyotrophic lateral sclerosis led to the discovery that beta-lactam antibiotics could increase the expression of neuronal glutamate transporter in cultured mammalian cells. Moreover, ceftriaxone (cephalosporin family) was found to protect animals from several forms of glutamate-induced toxicity (Rothstein et al. (2005) *Nature* 433, 73-77).

Previous reports have addressed the possibility of penicillin binding to plasma proteins, which was suspected as the initial step in the sequence of events leading to adverse hypersensitivity reactions associated with this antibiotic. For example, Christie et al. (1987) *Biochem Pharmacol,* 36, 3379-3385 have synthesized a conjugate of albumin and benzylpenicillin (also known as penicillin G), and investigated its disposition and metabolism. Bertucci et al. (2001) *Biochim Biophys Acta,* 1544, 386-392 have studied structural and binding properties of albumin modified with penicillin G.

Various uses of antibiotics including for applications other than treatment of bacterial infections have been proposed.

WO 2007/099396 discloses a therapeutic kit to provide a safe and effective dosage of an antibiotic agent, and a foamable composition including an antibiotic agent, at least one organic carrier, a surface-active agent, at least one polymeric additive and water. WO 2007/099396 further discloses a method of treating, alleviating or preventing disorders of the skin, body cavity or mucosal surface, wherein the disorder involves inflammation as one of its etiological factors, including administering topically to a subject having the disorder, a foamed composition including: an antibiotic agent, inter alia beta-lactam antibiotics, at least one organic carrier, a surface-active agent, a polymeric additive and water.

U.S. Pat. No. 6,627,625 discloses therapeutic methods using beta-lactam compounds including beta-lactam antibiotics and beta-lactamase inhibitors.

Antibiotics not containing beta-lactam moieties have been previously reported to affect apoptosis and cytokine secretion by T cells. Moxifloxacin, a fluoroquinolone antibiotic, was reported to inhibit TNFα and IL-6 secretion by T cells (Choi et al. (2003) *Antimicrob Agents Chemother,* 47, 3704-3707). Rifampicin, an antibiotic drug of the rifamycin group, was found to inhibit CD95-induced apoptosis by T cells (Gollapudi et al. (2003) *J Clin Immunol,* 23, 11-22), and macrolide antibiotics were reported to induce apoptosis in T cells (Ishimatsu et al. (2004) *Int J Antimicrob Agents,* 24, 247-253; and Kadota et al. (2005) *Int J Antimicrob Agents,* 25, 216-220). Minocycline was found to inhibit TNFα and INFγ (Kloppenburg et al. (1996) *Antimicrob Agents Chemother,* 40, 934-940), and doxycycline demonstrated anti-inflammatory effects (Krakauer et al. (2003) *Antimicrob Agents Chemother,* 47, 3630-3633).

Previous work on the effects of antibiotics on experimental autoimmune diseases has shown that minocycline, fucidin and tetracycline could inhibit experimental autoimmune encephalomyelitis (EAE) (Giuliani et al. (2005) *J Neuroimmunol,* 165, 83-91; Brundula et al. (2002) *Brain,* 125, 1297-1308; Di Marco et al. (2001) *Mult Scler,* 7, 101-104; and Popovic et al. (2002) *Ann Neurol,* 51, 215-223). Oral vancomycin, which is poorly absorbed, was found to inhibit adjuvant arthritis by its effects on the intestinal flora (Nieuwenhuis et al. (2000) *Arthritis Rheum,* 43, 2583-2589). Tetracycline is used clinically as an immune modulator in patients with Pemphigus and Bullous Pemphigoid (Calebotta et al. (1999) *Int J Dermatol,* 38, 217-221; and Kolbach et al. (1995) *Br J Dermatol,* 133, 88-90).

WO 2003/061605 discloses methods for treating a host suffering from a chronic immune disease, e.g., multiple sclerosis or chronic fatigue syndrome. In practicing the subject methods, an effective amount of an elastase inhibitory agent, e.g., a beta-lactam containing compound, is administered to the host. Compositions for use in practicing the subject methods are also disclosed.

WO 2011/047153 discloses methods for inhibiting pathways induced by commensal bacteria of the gastrointestinal (GI) tract that lead to Th 17 differentiation, which in turn leads to localized and systemic accumulation of Th17 cells that are causally associated with inflammatory and autoimmune disorders, and methods for identifying agents useful for treating non-gut autoimmune disorders. WO 2011/047153 discloses, inter alia, a method for treating a subject having a non-gut autoimmune disorder, the method comprising administering to the subject a therapeutically effective amount of an inhibitor of a Th17 cell inducing bacterial species.

Nowhere is it disclosed or suggested that certain beta-lactam antibiotics can directly and effectively down-regulate pro-inflammatory phenotypes of T cells. Particularly, none of the prior art discloses or suggests that ampicillin can inhibit the development of type I diabetes, even when administered in a sub-antibacterial amount that does not produce an antibacterial effect. There is a medical need for compositions and methods useful for type I diabetes therapy.

SUMMARY OF THE INVENTION

The present invention provides compositions and methods useful for the treatment of type I diabetes. The compositions and methods of the present invention utilize, in particular embodiments, the beta-lactam compound ampicillin that was surprisingly found to modulate T cells to inhibit the development of type I diabetes.

The present invention is based in part on the unexpected finding that administration of ampicillin to non-obese diabetic (NOD) mice, who spontaneously develop diabetes mellitus similar to type I diabetes in humans, resulted in a significantly reduced incidence of diabetes in these mice compared to non-treated mice and mice treated with a different beta-lactam antibiotic, as exemplified hereinbelow. Surprisingly, the effect was observed using a sub-antibacterial dosing regime of ampicillin. For example, the treated mice were injected subcutaneously at weekly intervals, rather than the normal anti-bacterial treatment regime for ampicillin. Gene expression analysis of human T cells upon incubation with ampicillin showed that this antibiotic induces changes in the expression of immune-related genes in the cells, characterized by up-regulation of genes known to participate in Th2 and Treg pathways.

According to one aspect, the present invention provides a method for treating or delaying the onset of type I diabetes in a subject in need thereof, the method comprising administering to the subject a pharmaceutical composition comprising ampicillin or a salt thereof.

Advantageously, ampicillin was found to induce its effect while administered in sub-antibacterial doses or sub-antibacterial treatment regimes, thus avoiding untoward effects on commensal bacteria and selection of resistant bacteria.

In some embodiments, the administered pharmaceutical composition comprises a sub-antibacterial dose of ampicillin. According to these embodiments, the antibiotic is present in the composition in an amount which is lower than that required for producing an effective antibacterial activity in a subject. For example, the composition may comprise about 90% or less, about 80% or less, about 70% or less, about 60% or less, about 50% or less, about 40% or less, about 30% or less, about 20% or less, about 10% or less, about 5% or less, of the antibacterial dose. Each possibility represents a separate embodiment of the invention.

In alternative or additional embodiments, the pharmaceutical composition comprising ampicillin is administered in a sub-antibacterial treatment regime. According to these embodiments, the antibiotic is administered in a treatment regime which is different from the typical anti-bacterial treatment regime known for this antibiotic, such that substantially no antibacterial effect is provided. For example, in some embodiments, the antibiotic is administered fewer times per day compared to the antibacterial treatment regime. In some exemplary embodiments, the antibiotic is administered in a frequency of less than once a day. In additional exemplary embodiments, the antibiotic is administered once every two or three days or less, or every 2-8 days. In yet additional exemplary embodiments the antibiotic is administered once a week.

In some embodiments, the pharmaceutical composition comprises an ampicillin derivative. In some embodiments, the ampicillin derivative is substantially devoid of antibacterial activity. In some exemplary embodiments, stereoisomers of ampicillin lacking antibacterial activity are used. The derivatives encompassed by the present invention include those that are capable of inhibiting the development of type I diabetes. In some embodiments, the derivatives encompassed by the present invention include those that are capable of inducing changes in the expression of immune-related genes in T cells, as detailed hereinbelow.

In alternative or additional embodiments, the administered composition comprises a complex or conjugate of ampicillin which is substantially devoid of antibacterial activity. In some embodiments, the antibiotic is conjugated to a protein. In some embodiments the protein is albumin. A conjugate of albumin and ampicillin may exhibit a longer half-life compared to the free antibiotic, therefore the use of such conjugate may provide prolonged therapeutic effect. Thus, the present invention further provides compositions and methods for the treatment of type I diabetes that utilize albumin-ampicillin conjugates.

In some embodiments, ampicillin is conjugated to albumin. According to these embodiments, the method comprises administering a pharmaceutical composition comprising as an active ingredient a conjugate of albumin and ampicillin.

In some typical embodiments, the albumin is human serum albumin.

As noted above, the conjugation to albumin may prolong the half-life of the antibiotic. Thus, a composition comprising an albumin-ampicillin conjugate may be administered, for example, only once a week or less, for example every 10 days or less. In some exemplary embodiments, the conjugate is administered once every 4-14 days. Each sub-range is within the scope of the present invention.

In some embodiments, the albumin-antibiotic conjugate is substantially devoid of anti-bacterial activity.

The method of the present invention provides treatment of type I diabetes. In some embodiments, treatment encompasses alleviation of symptoms and/or delay in disease progression. In some exemplary embodiments, treatment encompasses inhibition of disease progression in newly diagnosed type I diabetes patients. Thus, the method may be applied, in some embodiments, to a subject who is newly diagnosed with type I diabetes. For example, the method may be applied within 18-24 months or less, 10-18 months or less, 3-12 months or less, 1-2 months or less, from the diagnosis. Each possibility represents a separate embodiment of the invention. In some embodiments, treatment encompasses improvement in the disease state such that exogenous insulin requirements are reduced. In some embodiments, application of the method of the present invention reduces the loss of insulin producing cells in the pancreas.

In alternative or additional embodiments, treatment encompasses prophylactic treatment for subjects who are known to be at risk for developing type I diabetes.

The methods and compositions of the present invention utilize ampicillin in an amount which is effective to induce these effects.

In some embodiments, the subject is human. In other embodiments, the subject is a non-human mammal.

In some embodiments, ampicillin is administered in combination with another therapeutic agent, for example, an anti-diabetic agent. The method of the present invention may be combined with additional treatment or treatments.

According to another aspect, the present invention provides a pharmaceutical composition comprising ampicillin or a salt thereof, for use in the treatment or delaying the onset of type I diabetes.

In some embodiments, the composition further comprises a pharmaceutically acceptable diluent, solvent, excipient or carrier.

As exemplified hereinbelow, ampicillin was found to directly affect T cells and down-regulate pro-inflammatory phenotypes thereof. Thus, another way of treating a subject diagnosed with type I diabetes or is at risk of developing type I diabetes is an ex-vivo incubation of T cells collected from said subject with ampicillin, followed by re-infusion of the treated cells back to the subject.

According to a further aspect, the present invention provides a method for treating or delaying the onset of type I diabetes in a subject in need thereof, the method comprising (i) incubating T cells collected from the subject with ampicillin; and (ii) re-infusing said T cells to said subject.

In some embodiments, the T cells are activated by a mitogen prior to re-infusion to the subject. Examples of suitable mitogens include phytohemagglutinin (PHA), or phorbol myristate acetate (PMA) in combination with ionomycin or anti-CD3 antibodies. Mitogen stimulation of the T cells may be performed before incubation with the antibiotic, simultaneously or after incubation and before administration. Each possibility represents a separate embodiment of the invention. In some embodiments, the T cells are activated to up-regulate or enhance MHC class II expression.

In some embodiments, the T cells undergo antigen-specific activation prior to re-infusion to the subject. In some embodiments, T cells are isolated from the subject and those responsive to target antigens associated with type I diabetes, such as insulin, pro-insulin, glutamic acid decarboxylase (GAD), or HSP60, are selected and expanded by culture in vitro with the selected target antigens.

In some embodiments, the concentration of ampicillin which is incubated with the T cells ranges from about 15-100 µg/ml, for example, from about 20-75 µg/ml, from about 20-65 µm/ml, from about 25-55 µg/ml, from about 35-55 µg/ml. Each possibility represents a separate embodiment of the invention.

In some embodiments, the time of incubation of the beta-lactam compound with the T cells prior to administration to the subject ranges from 2-5 days, from 1-4 days. Each possibility represents a separate embodiment of the invention. In some particular embodiments, the time of incubation is 3 days.

In other embodiments, the time of incubation of the beta-lactam compound with the T cells prior to administration to the subject ranges from about 1-3 hours, from about 1.5-2.5 hours. Each possibility represents a separate embodiment of the invention. In some particular embodiments, the time of incubation is 2 hours.

In some embodiments, the number of T cells that are re-infused to the patient ranges from about $10^6$-$10^8$, for example, about $10^7$ cells. Each possibility represents a separate embodiment of the invention.

These and further aspects and features of the present invention will become apparent from the figures, detailed description, examples and claims which follow.

DETAILED DESCRIPTION OF THE INVENTION

Figure 1A:
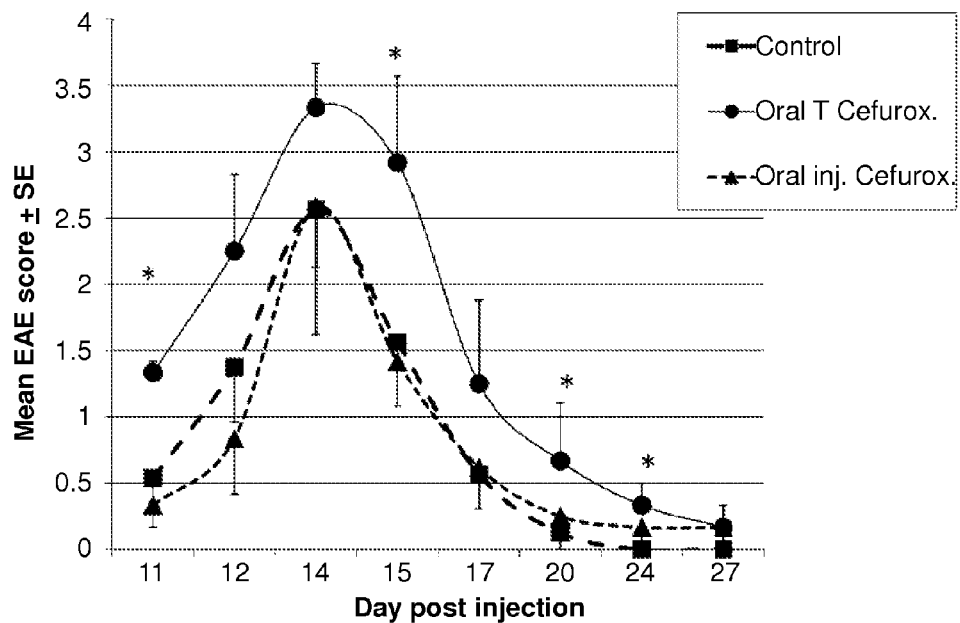
FIG. 1. Effects of beta-lactam antibiotics on experimental autoimmune diseases. A) Oral cefuroxime increases the severity of actively induced EAE. Asterisks indicate significant ($p<0.05$) changes between cefuroxime and control groups. B) Exacerbation of adjuvant-induced arthritis by cefuroxime treatment. C) Cefuroxime enhances the pathogenicity of the BP10 line. D) Inhibition of type I diabetes in NOD mice by ampicillin treatment.

The present invention is directed to the use of certain beta-lactam compounds in the treatment of type I diabetes. Particularly, the present invention is directed to the use of ampicillin, salts thereof and/or derivatives thereof in the treatment of type I diabetes.

The present invention is based in part on the unexpected finding that ampicillin can significantly inhibit the development of diabetes in a mouse model of type-I diabetes mellitus (DM). The effect is observed even for sub-antibacterial amounts of ampicillin.

The present invention is further based on the following findings that bear important clinical and fundamental implications:
1. Certain beta-lactam antibiotics can act as modulators of T-cell behavior;
2. Certain beta-lactam antibiotics, such as ampicillin, can down-regulate pro-inflammatory T-cell phenotypes; and
3. The immune modulation appears to be mediated by interaction of the beta-lactam molecule with albumin produced by the T cells.

It was previously suggested that beta-lactam antibiotics may inhibit certain autoimmune diseases, for example through inhibition of bacteria thought to be involved in the development of such diseases, e.g., arthritis. However, as exemplified hereinbelow, it was surprisingly found that ampicillin can inhibit the development of type I diabetes in a sub-antibacterial dosing regime. In addition, it was found that some beta-lactam antibiotics actually increase the severity of autoimmune diseases. As exemplified hereinbelow, ampicillin had no effect on the severity of other experimental autoimmune diseases, such as experimental autoimmune encephalomyelitis (EAE), in contrast to other beta-lactam antibiotics tested herein, that were found to increase the severity of the model diseases.

Albumin is widely known to be a blood protein produced by the liver and active in maintaining osmotic pressure in the vascular system and as a carrier for a variety of body molecules and drugs. Nevertheless, as exemplified hereinbelow, albumin expression was detected in several tissues and cells such as mesenchymal stem cells, dendritic cells, Jurkat, MOLT4, FAO and CEM lines. "Ectopic" albumin expression was previously described in healing bone, skin, granulosa cells, kidney and pancreas and mammary glands. Moreover, albumin was described to affect several biological processes: secretion of TGFβ1 by kidney tubular cells, and prevention of apoptosis in neuroblastoma cells, neuronal cells and CLL lymphocytes. In endothelial cells, albumin was found to activate the TGFβ receptor II and affect the phosphorylation and nuclear translocation of SMAD proteins. Other studies have found albumin to interact with DNA, transfer RNA and tumor associated peptides and proteins. Many pharmacological studies of albumin have identified the two major binding pockets of the molecule with specific endogenous and exogenous ligand-binding specific sites. There are earlier reports that penicillin binds covalently to albumin, and such binding affects the properties of albumin. However, albumin was not expected to be produced by immune cells or to acquire immune functions following an interaction with beta-lactams.

As further exemplified hereinbelow, albumin modified by a beta-lactam antibiotic is taken up by T cells, and the modified albumin affects T-cell gene expression and behavioral phenotype. The chemical modification of bovine serum albumin by n-acetylglucosamine was previously described as a signal for nuclear translocation. Indeed, proteomic studies have identified albumin within nuclei. Interestingly, six of the genes that were modified by beta-lactam treatment of human CD4 T cells were situated in the TGFβ pathway (Table 1 hereinbelow), similar to the documented effect of albumin on endothelial cells. The modification of TGFβ-related genes is likely to be important, as recent work implicates TGFβ signaling at the crossroads of T cell differentiation into both Th17 effector cells and Treg cells. As the half-life of penicillin-modified albumin is prolonged to 7 days compared to the half-life of free penicillin of 42 minutes, the biological effects of modified albumin are likely to be prolonged.

In vitro culture of many cellular systems, including T cells, B cells and dendritic cells, is dependent upon addition of serum (such as autologous serum or fetal calf serum) or components derived therefrom. Mesenchymal stem cells and the PC12 pheochromocytoma cell line are also dependent on serum for growth in culture, and BSA was found to affect gene expression and cardiomyocyte differentiation in human embryonic stem cells. Human T cell growth media that are serum-free (AIM-V, Invitrogen) contain human albumin; similarly, growth of human embryonic stem cells without serum necessitates albumin. Thus, it may be concluded that the presence of serum components and specifically albumin is important for cell survival and proliferation in many cell systems.

The data presented herein therefore documents novel and significant effects of beta-lactam antibiotics on T cell functions. Without wishing to be bound by any particular theory or mechanism of action, the effect may involve chemical modification of albumin, leading to widespread changes in cellular genes resulting in a change in T cell behavior.

According to one aspect, the present invention provides a method for treating type I diabetes in a subject in need thereof. In some embodiments, a method for treating a subject newly diagnosed with type I diabetes is provided. In some embodiments, a method for delaying the onset of type I diabetes in a subject at risk thereof is provided.

In some embodiments, the methods comprise administering to the subject a pharmaceutical composition comprising ampicillin. In alternative or additional embodiments, the method comprises administering a pharmaceutical composition comprising a salt of ampicillin.

Type 1 diabetes signs and symptoms typically include increased thirst and frequent urination, extreme hunger, weight loss, fatigue and/or blurred vision. Type I diabetes testing and diagnosis may be based on at least one of the following:

Glycated hemoglobin (A1C) test, where the average blood sugar levels for the two-three months prior to the test is assessed based on the measurement of the percentage of blood sugar attached to hemoglobin. An A1C level of 6.5 percent or higher on two separate tests is usually indicative of diabetes. A result between 5.7 and 6.4 percent is considered pre-diabetes, and indicates a high risk of developing diabetes.

Random blood sugar test. Blood sugar values are typically expressed in milligrams per deciliter (mg/dL) or millimoles per liter (mmol/L). Regardless of the type of food consumed by the tested individual prior to the test, a random blood sugar level of 200 mg/dL (11.1 mmol/L) or higher is suggestive of diabetes, especially when coupled with any of the signs and symptoms of diabetes as noted above. A level between 140 mg/dL (7.8 mmol/L) and 199 mg/dL (11.0 mmol/L) is considered pre-diabetes, and indicates a high risk of developing diabetes.

Fasting blood sugar test. A blood sample is taken after an overnight fast. A fasting blood sugar level less than 100 mg/dL (5.6 mmol/L) is considered normal. A fasting blood sugar level from 100 to 125 mg/dL (5.6 to 6.9 mmol/L) is considered pre-diabetes. A fasting blood sugar level of 126 mg/dL (7 mmol/L) or higher on two separate tests is usually indicative of diabetes.

Additional tests used for testing type I diabetes include determining the presence of auto-antibodies common in type 1 diabetes in the blood of the subject, and the presence of ketones in the urine.

Another test that may be used is serum levels of C-peptide, a known marker of insulin production and surviving β-cells. Normal C-peptide levels following fast are generally considered to be between 0.5 nanograms (ng) per milliliter (ml) and 3 ng/ml. Significantly lower amounts of C-peptide in the blood are suggestive of type I diabetes.

According to a further aspect, the present invention provides a method for treating diabetes in a subject in need thereof, the method comprising: infusing to the subject T cells obtained from said subject and incubated ex vivo with ampicillin.

In some embodiments, the method comprises: (i) collecting T cells from the subject; (ii) incubating the T cells with ampicillin; and (iii) re-infusing said T cells to said subject.

In some embodiments, collecting T cells from the subject comprises collecting a sample of peripheral blood from the subject, and purifying the T cells from the blood sample. Methods for purifying T cells are known in the art, an exemplary procedure is described in the Examples section below. T cells may also be collected by lymphopheresis, as known in the art. In some embodiments, the collected T cells are subjected to further separation processes, for example, to isolate $CD4^+$ T cells.

In some embodiments, the T cells are activated by a mitogen prior to re-infusion to the subject. Examples of suitable mitogens include phytohemagglutinin (PHA), phorbol myristate acetate (PMA) plus ionomycin and anti-CD3 antibodies. An exemplary procedure for activating T cells is described in the Examples section below. In some embodiments, the T cells undergo antigen-specific activation prior to re-infusion to the subject. In some embodiments, T cells are isolated from the subject and those responsive to target antigens associated with type I diabetes, such as insulin, pro-insulin, glutamic acid decarboxylase (GAD), or HSP60, are selected and expanded by culture in vitro with the selected target antigens.

Stimulation of the T cells may be performed before incubation with the antibiotic, simultaneously or after incubation and before administration. Each possibility represents a separate embodiment of the invention. In some embodiments, the T cells are activated to up-regulate or enhance MHC class II expression, as known in the art.

The concentration of ampicillin which is incubated with the T cells may range from about 15-60 µg/ml, for example, from about 20-55 µg/ml, from about 25-50 µg/ml, from about 40-55 µg/ml. Each possibility represents a separate embodiment of the invention.

As used herein, the term "about", when referring to a measurable value such as an amount, a temporal duration, and the like, is meant to encompass variations of .+−.10%, more preferably .+−.5%, even more preferably .+−.1%, and still more preferably .+−.0.1% from the specified value, as such variations are appropriate to perform the disclosed methods.

The time of incubation of the beta-lactam compound with the T cells prior to administration to the subject may range from about 2-5 days, from about 3-6 days, from about 1-4 days. For example, the time of incubation may be about 3 days. Each possibility represents a separate embodiment of the invention.

Alternatively, the time of incubation of the beta-lactam compound with the T cells prior to administration to the subject may range from about 1-3 hours, from about 1.5-2.5 hours. For example, the time of incubation may be about 2 hours. Each possibility represents a separate embodiment of the invention.

The number of T cells that are re-infused to the patient may range from about $10^6$-$10^8$, for example, about $10^7$ cells. Each possibility represents a separate embodiment of the invention.

According to another aspect, the present invention provides a pharmaceutical composition comprising ampicillin or a salt thereof, for use in the treatment of type I diabetes.

In some embodiments, the composition further comprises a pharmaceutically acceptable diluent, solvent, excipient or carrier.

In some embodiments, treatment encompasses improvement in the disease state such that exogenous insulin requirements are reduced. In some embodiments, improvement in the disease state is reflected by improvement in the indices noted above, such as A1C test and blood sugar test. In some embodiments, treatment encompasses maintaining persistence production of C-peptide. In some embodiments, the use of ampicillin, salts thereof and/or derivatives thereof according to embodiments of the present invention reduces or even arrests the loss of insulin producing cells in the pancreas.

In some embodiments, treatment comprises inhibition of disease progression in newly diagnosed type I diabetes patients. In some embodiments, the method is applied to a subject who has been recently diagnosed with type I diabetes, for example, within 18-24 months or less, 10-18 months or less, 3-12 months or less, 1-2 months or less, from the diagnosis. Each possibility represents a separate embodiment of the invention.

In some embodiments, subjects amenable to treatment by the methods of the present invention are newly diagnosed type I diabetes patients that show detectable levels of C-peptide in their blood.

Inhibition of disease progression may include arresting the loss of insulin producing cells in the pancreas, as may be reflected by, e.g., persistence production of C-peptide, balanced levels of blood glucose and/or reduced need of exogenous insulin.

In some embodiments, the subject is human. In other embodiments, the subject is a non-human mammal.

In alternative or additional embodiments, treatment encompasses prophylactic treatment for subjects who are known to be at risk for developing type I diabetes. Subjects at risk may be identified, for example, by the presence of anti-insulin, anti-GAD and/or anti-islet cell antibodies. Subjects at risk may also include first degree relatives of patients with positive antibodies to insulin, GAD, and islet cell antigens.

Thus, according to another aspect, the present invention provides a method for delaying the onset of type I diabetes in a subject, the method comprising administering to the subject a pharmaceutical composition comprising ampicillin or a salt thereof.

As used herein, "delaying the onset" encompasses inhibiting or even preventing the appearance of clinical symptoms of type I diabetes.

In some embodiments, the method is applied to a subject at risk of developing type I diabetes, which may be identified according to the parameters detailed above.

The method is typically applied to a subject that does not present clinical symptoms of type I diabetes. For example, in some embodiments, the subject does not show unbalanced blood glucose levels. In alternative or additional embodiments, the subject does not show signs of beta-cell destruction in the pancreas.

The beta-lactam antibiotic or salts thereof utilized according to embodiments of the present invention are commercially available, and may also be synthesized using methods known in the art. Ampicillin may be identified by CAS registry number 69-53-4. Information about the chemistry and synthesis of beta-lactam compounds can be found, for example, in Bruggink (ed.) Synthesis of β-lactam antibiotics: chemistry, biocatalysis & process integration, 2001, Springer; and Page (ed.) The Chemistry of [beta]-lactams, 1992, Blackie Academic & Professional.

In some embodiments, pharmaceutically acceptable salts of ampicillin are used. Non-limiting examples of suitable salts include sodium and potassium salts. Pharmaceutically acceptable salts utilized according to embodiments of the present invention are salts that do not substantially contribute to the toxicity of the compound. Such salts can be formed by well known procedures.

In some embodiments, ampicillin is conjugated to, or complexed with, albumin. According to these embodiments, the methods of the present invention comprise administering a pharmaceutical composition comprising as an active ingredient a conjugate of albumin and ampicillin.

In some typical embodiments, the albumin is human serum albumin.

Advantageously, the conjugation to albumin may prolong the half-life of the beta-lactam compound. Thus, the treatment regime with a composition comprising an albumin-beta-lactam conjugate may include fewer administrations per a given period of time compared to that of a free beta-lactam antibiotic.

In some embodiments, the albumin-antibiotic conjugate is substantially devoid of anti-bacterial activity.

As used herein, the "substantially devoid of anti-bacterial activity" indicates no or only negligible activity, of no clinical significance.

Albumin, including human serum albumin, is commercially available, and may also be synthesized using, e.g., recombinant methods known in the art. In order to prepare an albumin-beta-lactam conjugate, the two components may be mixed and incubated. For example, the two components may be mixed at an alkaline pH, which favors a reaction between the beta-lactam compound and amino groups in lysine residues of the protein.

It was surprisingly found that the beta-lactam antibiotic according to embodiments of the present invention exerts its activity towards T cells even when administered in an amount which is less than that required for producing a clinically effective anti-bacterial activity, namely, a sub-antibacterial amount. Thus, in some embodiments, the antibiotic is administered such that substantially no antibacterial effect is obtained.

In some embodiments, a sub-antibacterial dose of the antibiotic is administered. According to these embodiments, the antibiotic is present in the composition in an amount which is lower than that required for producing an effective antibacterial activity in a subject. For example, the composition may comprise about 90% or less, about 70% or less, about 50% or less, about 30% or less, about 10% or less of the antibacterial dose. Each possibility represents a separate embodiment of the invention. For example, ampicillin for oral administration for human is available, inter alia, as capsules containing 250 mg of the antibiotic. In some exemplary embodiments, a pharmaceutical composition for oral administration may comprise about 225 mg ampicillin or less, about 175 mg or less, about 125 mg or less, about 75 mg or less, about 25 mg or less. Each possibility represents a separate embodiment of the invention.

In alternative or additional embodiments, the antibiotic is administered in a treatment regime that is different from the typical anti-bacterial treatment regime known for the antibiotic, such that substantially no antibacterial effect is provided. For example, the antibiotic may be administered fewer times per day compared to the antibacterial treatment regime. In some embodiments, the antibiotic is administered in a frequency of less than once a day. In some exemplary embodiments, the antibiotic is administered once every two or three days or less, or every 2-8 days. Each possibility represents a separate embodiment of the invention. In additional exemplary embodiments the antibiotic is administered once a week.

In some embodiments, a derivative of ampicillin is used. In some embodiments, a substantially non-antibacterial derivative ampicillin is used. In some exemplary embodiments, a stereoisomer of ampicillin is used.

The compounds and derivatives encompassed by the present invention include those that are capable of inhibiting the development of type I diabetes. In some embodiments, the derivatives encompassed by the present invention include those that are capable of inducing changes in the expression of immune-related genes in T cells, as detailed hereinbelow.

The ability of a compound to modulate T cell activity according to embodiments of the present invention may be determined using an in vitro assay testing the effect of a given compound on expression of immune-related genes in T cells, for example using the gene array described in the Examples section hereinbelow. In order to test a compound, purified T cells are stimulated in the presence of the compound and the effect on gene expression is then determined. An exemplary procedure is described hereinbelow. Compounds that up-regulate the expression of the genes listed in Table 1 hereinbelow, or a significant portion thereof, may be suitable for use according to embodiments of the present invention. Alternatively, compounds that up-regulate the expression of the following genes may also be suitable: CCR4, ACVR2, JAK1, STAT4, TLR2 and NFKBIE.

The ability of a compound to modulate T cell activity according to embodiments of the present invention may also be determined, for example, using an in vivo assay testing the effect of a given compound on the development of autoimmune diabetes in NOD mice. In order to test a compound, NOD mice are administered with the compound and the development of diabetes in the mice is monitored for a given period of time. An exemplary procedure is described in the Examples section hereinbelow. Compounds whose administration to the mice results in a lower incidence of diabetes compared to non-treated mice may be suitable for use according to embodiments of the present invention.

In some embodiments, a complex or conjugate of the beta-lactam antibiotic which is substantially devoid of antibacterial activity is used. In some embodiments, the antibiotic is conjugated to, or complexed with, a protein, for example, albumin.

Various assays are known in the art for testing antibacterial activity of a given compound, e.g. zone of inhibition screening test or agar disc diffusion method. Such assays may be applied to the derivatives and/or conjugates according to embodiments of the present invention to determine their antibacterial activity, if any.

Ampicillin, salts thereof and/or derivatives thereof are utilized herein for the treatment of type I diabetes.

In some embodiments, ampicillin is administered in combination with another therapeutic agent, for example, an anti-diabetic agent. As used herein, "in combination" includes both sequential and concurrent administration of the different active agents. The method of the present invention may be combined with additional treatment or treatments.

Pharmaceutical compositions of the present invention preparations of one or more active ingredients with other chemical components such as physiologically acceptable carriers and excipients. The purpose of a pharmaceutical composition is to facilitate administration of a compound to an organism.

As used herein, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered active agent.

As used herein, the term "excipient" refers to an inert substance added to a pharmaceutical composition to further facilitate administration of an active ingredient. Non-limiting examples of excipients include calcium carbonate, calcium phosphate, various sugars and types of starch, cellulose derivatives, gelatin, vegetable oils, and polyethylene glycols. Techniques for formulation and administration of drugs may be found in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000). Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are particularly suitable for administration systemically. Systemic administration includes all enteral and parenteral routes. Non-limiting examples of suitable administration routes include oral, rectal, transmucosal such as transnasal and buccal, intravenous, intramuscular, transdermal, subcutaneous, intradermal, intravesicular and inhalation routes. Typically, the pharmaceutical compositions of the present invention are administered by oral or intravenous routes. The appropriate rout of administration and formulation may be determined, in some embodiments, according to the properties of the active ingredient. For example, where the active ingredient is a conjugate of a beta-lactam compound and a protein, for example a beta-lactam-albumin conjugate, the proper formulation may be for parenteral administration, e.g. injection.

For injection, the active ingredients of the pharmaceutical composition may be formulated in aqueous solutions, preferably in physiologically compatible buffers such as Hank's solution, Ringer's solution, or physiological salt buffer. Pharmaceutical compositions for potential administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added. Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Alternative embodiments include depots providing sustained release or prolonged duration of activity of the active ingredient in the subject, as are well known in the art.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein.

The present invention further provides kits. In some embodiments, a kit is provided, for treating type I diabetes in a subject. In some embodiments, the kit comprises a composition comprising ampicillin, salts or derivatives thereof, and may also include instructions for administering said composition to a subject in need thereof. Such instructions may include, for example, a dosing regimen. In some embodiments, the kit comprises means for administering the composition or compositions. For example, for injection administration, the kit may include a syringe.

In some embodiments, a kit for in vitro/ex vivo treatment of T is provided. In some embodiments, the kit comprises ampicillin, salts or derivatives thereof. Such kit may further include at least one of means for collecting a blood sample from a subject, means for isolating T cells from a blood sample, and means for re-infusing the treated T cells back to the subject. For example, the kit may include syringes, tubes, infusion bags, collection bags. The kit may further include instructions for performing the ex-vivo procedure.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods

Animals:

Inbred female Lewis rats and NOD (non-obese diabetic) mice were supplied by the animal breeding center of the Weizmann Institute of Science, Israel, under the supervision of Harlan Laboratories and were used at 2-3 months of age. Experiments were approved by the Institutional Animal Care and Use Committee. Human peripheral blood lymphocytes from healthy donors were obtained from the blood bank of Sheba Medical Center, Tel Hashomer, Israel.

Reagents, Antigens and Antibodies:

*Mycobacterium tuberculosis* H37Ra was purchased from Difco (Detroit, Mich.). Guinea-pig myelin basic protein and Concanavalin A (ConA) were purchased from Sigma (Rehovot, Israel). Antibiotics were purchased from a local pharmacy. Anti-human CD3 (OKT3, eBioscience, San Diego, Calif.) was used to coat 24 well plates at 2 µg/ml in PBS. Rabbit polyclonal anti-human serum albumin was purchased from SIGMA (Rehovot, Israel, Catalogue number A0433). Mouse monoclonal anti-penicillin (Pen 9) was from AbD-Serotec (Oxford UK). Captavidin was from Invitrogen, (Carlsbad, Calif. USA) and Sulfo-NHS-LC Biotin was from Pierce (Rockford, Ill., USA).

Realtime PCR primers for rat albumin were: forward primer CCCGATTACTCCGTGT (SEQ ID NO.: 1); reverse primer: TGGCGTTTTGGAATCCATA (SEQ ID NO.: 2). Human primers for albumin were forward ATGCGCTATT-AGTTCGTTAC (SEQ ID NO.: 3); reverse primer CATG-GTCGCCTGTTCA (SEQ ID NO.: 4).

Radioactive $^3[H]$ benzylpenicillin was purchased from Amersham (Buckinghamshire, UK; 250 µCi, 1 mCi/ml). Human albumin was from Calbiochem (Merck Darmstadt, Germany).

T-Cell Lines:

Antigen-specific T-cell lines were established from lymph node cells that had been stimulated with myelin basic protein (MBP; 10 µg/ml) for 3 days in stimulation medium as described below. Following stimulation, the T-cell blasts were isolated on LYMPHOPREP™ (Nycomed Pharma, Oslo, Norway) and seeded in propagation medium. Propagation medium was identical to stimulation medium without autologous serum, but supplemented with fetal calf serum 10% and T-cell growth factors from the supernatant of Con A stimulated spleen cells 10% (Mor et al. (1990) *J Clin Invest,* 85, 1594-1598). Animals were injected intra-peritoneally with 107 MBP-stimulated T cells, following 6-8 cycles of in vitro stimulations. It is known that MBP-reactive lines undergo a reduction in pathogenicity after 6 or more in vitro stimulations. In some experiments the BP10 line was stimulated with phorbol myristate acetate (PMA; 50 ng/ml) and ionomycin (500 ng/ml) for 3 days in stimulation medium, without antigen-presenting cells.

Induction of EAE:

Active EAE was induced by subcutaneous injection of 25 µg guinea-pig MBP (GpMBP) in complete Freund's adjuvant (CFA). CFA was prepared by adding 4 mg/ml *Myco-* bacterium tuberculosis H37Ra (Difco, Mich.) to incomplete Freund's adjuvant (IFA). Adoptive EAE was transferred by intra-peritoneal injection of guinea-pig MBP-activated cells of the BP10 line as described in Mor et al. (1993) *J Clin Invest*, 92, 2199-2206. Clinical EAE was observed 4-6 days following administration of T-cell line and 11-12 days following GpMBP/CFA injection. Clinical scoring was: +1, paralysis of tail; +1.5, paresis of posterior paws and ataxia; +2, paraplegia; +3, paralysis extending to thoracic spine; +4, a moribund state.

AA Induction and Assessment:

Heat-killed *Mycobacterium tuberculosis* (Mt) strain H37Ra (Difco) was finely ground using a pestle and mortar, and was suspended to a final concentration of 10 mg/ml in IFA. Test rats were injected at the base of the tail with a total of 100 µl of the Mt suspension. The day of AA induction was designated as day 0. Disease severity was assessed by direct observation of all four limbs in each animal. A relative score between 0 and 4 was assigned to each limb based on the degree of joint inflammation, redness, and deformity; thus, the maximum possible score for an individual animal was 16. The results are presented as the mean±SE of total score.

Radioactive Penicillin Binding Assay:

Tritium labeled benzylpenicillin was obtained from Amersham (Buckinghamshire, UK; 250 µCi, 1 mCi/ml). Human CD4 or CD8 T cells were stimulated in 24 well plates, $5 \times 10^6$ cells per ml, with PMA and Ionomycin for 72 hr in the presence of 10 or 20 µCi of labeled penicillin. Following stimulation, the cells were collected, lysed and separated by SDS PAGE. The gels were fixed, treated with 1M sodium salicylate, and dried. The dried gels were exposed to x-ray film (BioMax MS film) for 14 days, with intensifying screen (BioMax TranScreen, Eastman Kodak Co., New Haven Conn., USA), and were developed.

Human T Cells:

T cells were purified from the peripheral bloods of healthy human donors (Blood Bank, Sheba Medical center). The whole blood was incubated (20 min, 22° C.) with RosetteSep™ human T cell enrichment mixture (StemCell Technologies, Vancouver, Canada). The remaining unsedimented cells were then loaded onto lymphocyte separation medium (ICN Biomedicals, Irvine, Calif.), isolated by density centrifugation, and washed with PBS. The purified cells were 95% $CD3^+$ T cells. In a second round of purification, $CD3^+$ T cells were labeled for selection with a magnetically coupled mAb against CD4 (Miltenyi Biotec, Auburn, Calif.). The purified cells obtained (usually 97% $CD4^+$ T cells) were cultured in RPMI 1640 medium containing 10% heat-inactivated FCS.

Western Blot:

Rat tissues were ground with a tissue grinder in lysis buffer. The homogenate was centrifuged 14000 g for 15 min in 4° C. and the supernatant was used for western blotting. The protein concentration was determined using the BIO-RAD DC™ protein assay (Bio-Rad laboratories, Hercules, Calif.). Following electrophoresis in SDS gel in a mini-gel apparatus (Bio-Rad), the gels were electro-transferred to nitrocellulose membranes (Schleicher and schuell, Dassel, Germany). The nitrocellulose membranes were washed with distilled water for 5 min, and then blocked for 60 min. using a blocking solution composed of 2% bovine serum albumin (Fraction V, Sigma, St. Louis Mo.), 2.5% milk powder (Bio-Rad), Tris (Sigma) pH 7.5 10 mM, NaCl 150 mM and 0.02% thimerosal (Sigma). After 3×10 min. washes in PBS/TWEEN® 20 (PBS/T; 0.02%, Sigma), primary antibodies (1/1000) were incubated with the membranes in PBS/TWEEN® for 60 min. Following another series of washes in PBS/T (3×10 min), the membranes were incubated with a secondary antibody (Peroxidase conjugated anti rabbit or anti mouse, IgG Jackson ImmunoResearch, West Grove, Calif.) at a 1/2500 dilution in 2% milk in PBS solution for 60 min. After another 3×10 min washes, the membranes were incubated with the ECL reagent (for 60 seconds) and exposed to X-ray film.

Immunoprecipitation:

For immunoprecipitation experiments, T cells were incubated with penicillin (50 µg/ml), for the times indicated and then lysed in lysis buffer. Lyzates were incubated with rabbit polyclonal antibody to human serum albumin (Sigma, 1 hr RT). Next, we incubated the mixture with Protein A sepharose for 1 hr, and after 3 washes in PBS the bound proteins were eluted with sample buffer by heating to 95° C. for 5 min and run in SDS gels. The 67 kD band was excised, digested with trypsin and subjected to mass spectrometry as described in Mor et al. (2005) *J Immunol*, 175, 3439-3445.

Gene-Array Experiments:

Human CD4 T cells were isolated as described, and incubated in 24 well plates (Nunc), $4 \times 10^6$ cells/ml with plate bound anti-human CD3 (OKT3) at 2 µg/ml. The stimulation was performed in RPMI medium supplemented with 0.1% BSA. After 2 hours of stimulation with or without cefuroxime (50 µg/ml) or ampicillin (50 µg/ml), cells were collected washed and suspended in TRI REAGENT (Molecular research center, Cincinnati, Ohio). RNA was extracted from samples and used to prepare probes for gene array in accord with the manufacturer's instructions (SuperArray Bioscience, Frederick, Md.). Adequate labeling of the probes was tested before hybridization. Three healthy donors were tested in stimulation with cefuroxime. The membranes were analyzed online with the Image Data Acquisition and Expression Analysis (SuperArray Bioscience).

Real-Time PCR Analysis:

To verify the results of the gene array, we synthesized real-time PCR primers (designed with the LIGHTCYCLER® probe design software (Roche)). Real-time PCR of 6 selected genes was performed using a LIGHTCYCLER® (Roche, Basel, Switzerland). RNA was reverse transcribed to cDNA from 1 µg of total RNA, which was then subjected to quantitative RT-PCR performed essentially according to the manufacturer's instructions. Specific primer pairs were used to amplify specific genes in the presence of 3 mM MgCl2. PCR was performed in triplicate in a total volume of 20 µl of LIGHTCYCLER® HotStart DNA SYBR Green I mix (Roche) containing primer and 5 µl of cDNA. PCR amplification was preceded by incubation of the mixture for 10 min at 95° C., and the amplification step consisted of 45 cycles of denaturation, annealing, and extension. Denaturation was performed for 15 s at 95° C., annealing was performed in 60° C., and the extension was performed at 72° C. for 20 s, with fluorescence detection at 72° C. after each cycle. After the final cycle, melting point analyses of all samples were performed within the range of 62-95° C. with continuous fluorescence detection. A standard curve was generated from one sample in each run. Expression levels of β2-microglobulin (B2M) were used for sample normalization (β-actin levels were affected by cefuroxime treatment). The primer sequences were:

B2M sense TAGCTCTAGGAGGGCTG (SEQ ID NO.: 5) anti-sense ACCACAACCATGCCTTA (SEQ ID NO.: 6); ACVR2 sense ATCTCCGCGTAAGGAA (SEQ ID NO.: 7), anti-sense TGGGACTAACAATCGTG (SEQ ID NO.: 8); CCR4 sense TCCTAGAGACCCTGGTG (SEQ ID NO.: 9), anti-sense GGACTGCGTGTAAGATG (SEQ ID NO.: 10); JAK1 sense AGGAGTATTACACCGTCAAG (SEQ ID NO.: 11), anti-sense GGGTTGGGCCTATCAT (SEQ ID NO.: 12); STAT4 sense ACATCCTGCGAGACTAC (SEQ ID NO.: 13), anti-sense CACCGCATACACACTT (SEQ ID NO.: 14); TLR2 sense CTTCTGGAGCCCATTG (SEQ ID NO.: 15), anti-sense ACGGTACATCCACGTAG (SEQ ID NO.: 16); NFKBIE sense GACTTTGTGGTAGAGGCA (SEQ ID NO.: 17), anti-sense AAAACGTGGAGTCAGC (SEQ ID NO.: 18).

Results for each gene are presented as the relative expression level compared with B2M. Comparison between membranes was performed after normalization in accord with the manufacturer instructions.

Statistical Analysis:

The animal disease scores were compared using Mann-Whitney test.

Example 1

Effect of Different Beta-Lactam Antibiotics on the Severity of EAE and AA

Several beta-lactam antibiotics were tested for their effect on active experimental autoimmune encephalomyelitis (EAE), adoptive EAE and/or adjuvant arthritis (AA).

Figure 1B:
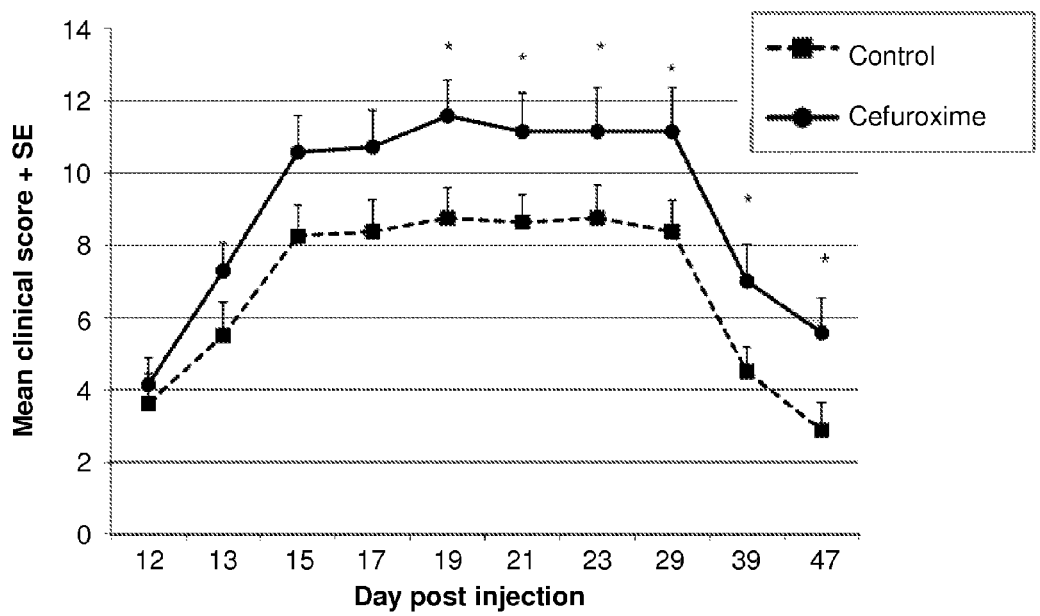

The first antibiotic that was tested is cefuroxime. To test the effects of antibiotics in vivo, active EAE was induced in rats as described above, and the injected rats (4 per group) were treated with oral cefuroxime Axetil™ in the drinking water from day 7 post-induction ("Oral T Cefurox."). One 500 mg tablet was dissolved in 500 ml of drinking water. The daily dose was 50 mg/kg, in the range of therapeutic pediatric human doses. As a control, the intravenous cefuroxime sodium preparation, which is not absorbed into the circulation, was administered orally ("Oral inj. Cefurox."). A second control group was given water without antibiotics ("Control"). As can be seen in FIG. 1A, the rats that received oral cefuroxime developed significantly more severe EAE than the two control groups. To extend the results to another experimental autoimmune disease, Adjuvant Arthritis (AA), two groups of 8 rats each were injected with CFA. On day 12 post-injection the rats were divided into two groups with similar disease scores. One group was injected IP with cefuroxime 5 mg (25 mg/kg) on the days indicated in the graph presented in FIG. 2B, and the second group was non-injected and served as a control. The chosen treatment regime, once every 2 or 3 days, was different from the anti-bacterial dosing regime (3 daily injections), in order to differentiate the immuno-modulating effect from an antibacterial effect. As can be seen in FIG. 1B, the rats that had been injected with cefuroxime showed significantly more severe arthritis scores compared to the control group. Thus, the enhancing effects of cefuroxime were manifested in two experimental autoimmune diseases.

Figure 1C:
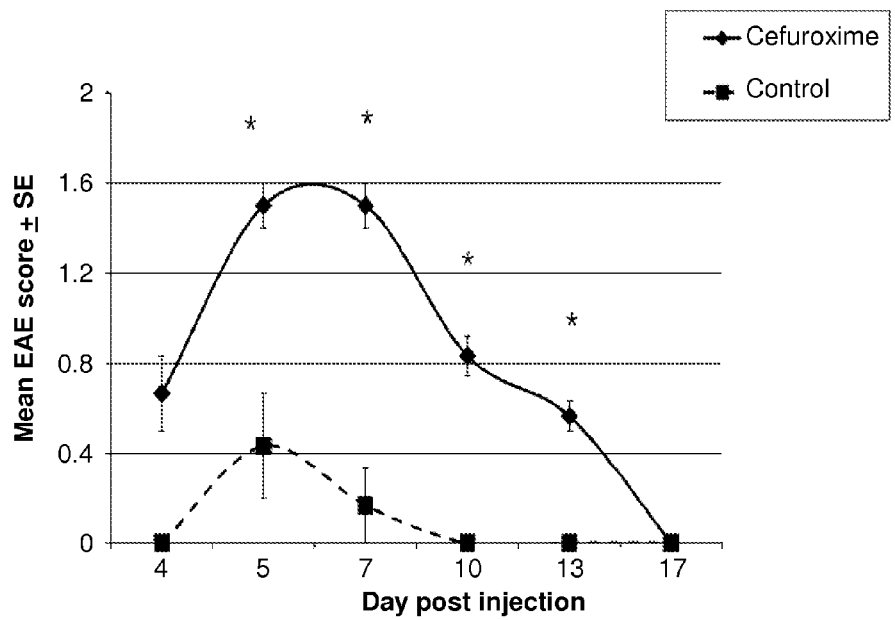

Treatment with cefuroxime in vivo could affect many different host agents involved in EAE or AA as well as influencing the rats' bacterial flora. To test whether the antibiotic might directly modify the behavior of effector T cells, an encephalitogenic T-cell line was stimulated in the presence or absence of cefuroxime in vitro. The weakly encephalitogenic BP10 line was used, and was stimulated for 3 days with MBP in the presence or absence of cefuroxime (50 µg/ml). The activated T cells were then washed to remove the antibiotic, the T cells were injected intraperitoneally into naïve recipient rats ($10^7$ per rat), and EAE was scored. The BP10 line at later stimulations was used, when its pathogenic potential is reduced, allowing to detect both suppression and enhancement of disease. As can be seen in FIG. 1C, the presence of cefuroxime during T-cell activation markedly enhanced the manifestations of EAE in the recipient rats. A dose-response experiment showed that cefuroxime at 5 µg/ml was ineffective, but 25 µg/ml had an enhancing effect similar to that of 50 µg/ml. A similar enhancing effect was seen upon incubation of the BP10 line with 50 µg/ml of another beta-lactam antibiotic, penicillin. To rule out antigen presenting cells (APC) as the target of the beta-lactam antibiotic, the encephalitogenic BP10 line was stimulated without APC using PMA (50 ng/ml) and Ionomycin (500 ng/ml) in the presence or absence of cefuroxime. The EAE mediated by the T cells stimulated in the presence of cefuroxime was significantly more severe, indicating that the antibiotic directly affected the encephalitogenic T cells.

Additional beta-lactam antibiotics were tested for their effect on the adoptive transfer of EAE. The BP10 line was incubated with ceftriaxone or ampicillin (at 50 µg/ml). Ceftriaxone enhanced EAE severity, as did cefuroxime, but ampicillin treatment did not increase the severity of EAE.

Example 2

Ampicillin Protects NOD Mice from Diabetes

Figure 1D:
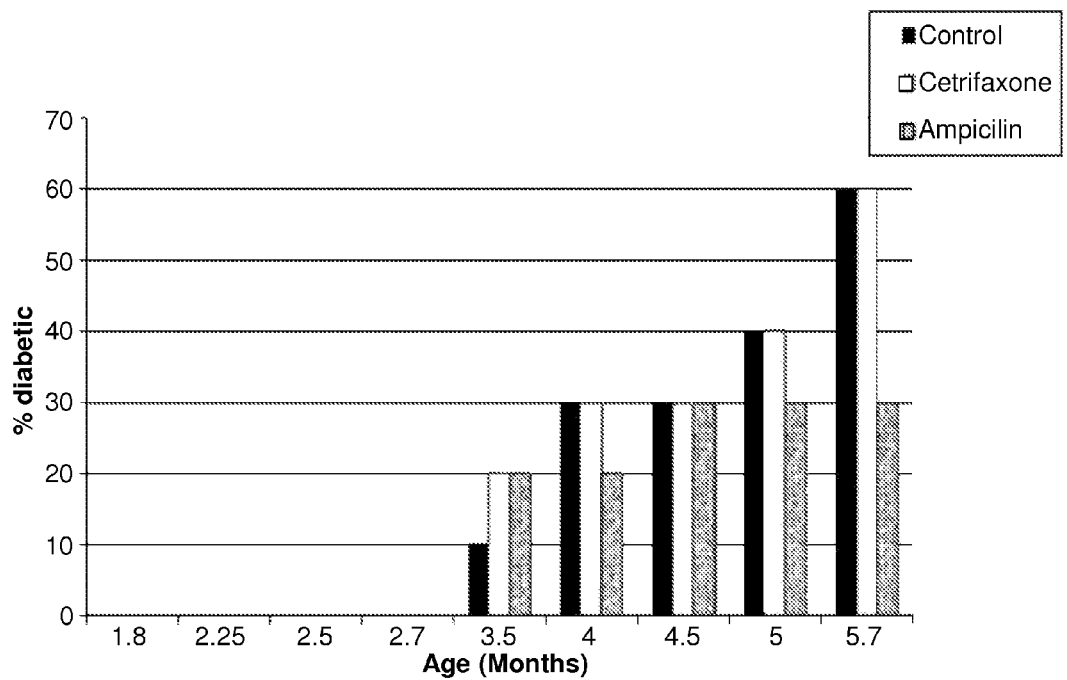

NOD mice spontaneously develop diabetes mellitus similar to type I diabetes in humans. Since ceftriaxone enhanced EAE, but ampicillin did not, the effects of the two beta-lactam antibiotics on the development of autoimmune diabetes in NOD mice was tested. Groups of 10 mice were untreated or injected subcutaneously at weekly intervals (instead of the known antibacterial treatment regime of 3 intravenous injections per day) with either ceftriaxone (675 µg per mouse) or ampicillin (at a dose of 1300 µg per mouse). The mice were followed for the development of diabetes, marked by blood sugar above 300 mg/dl on 2 measurements. The mice treated with ampicillin developed an incidence of diabetes of 30% at 5.7 months; while the control and ceftriaxone-injected mice manifested a 60% incidence of disease (FIG. 1D; P=0.05 control versus ampicillin and p=0.017 ceftriaxone versus ampicillin). Thus, some beta-lactam antibiotics can have opposing effects on different T-cell mediated autoimmune diseases in rodents: ampicillin down-regulates NOD mouse diabetes, but not rat EAE, and ceftriaxone up-regulates rat EAE, but not mouse diabetes.

Example 3

Cefuroxime and Ampicillin Manifest Opposing Effects on Immune-Related Gene Expression in Human T Cells The Human Autoimmune and Inflammatory Response Gene Array (SuperArray Bioscience corporation, Frederick, Md., USA) was used for analysis of gene expression by the T cells. This array contains 367 genes including cytokines, chemokines and their receptors, transcription factors and signaling proteins. CD4+ T cells were purified from healthy human donors, stimulated for 120 min with mitogenic plate-bound anti-CD3 antibody in the presence or absence of cefuroxime 50 µg/ml or ampicillin 50 µg/ml, and the effect on gene expression was analyzed. Analysis of the results was performed using the GEArray analysis program. The results are shown in Table 1 hereinbelow. Fifty-seven genes were found to be down-regulated by cefuroxime ("Cef"); but most of these genes (56 of the 57) were up-regulated by ampicillin ("Amp"). Interestingly, 8 of these genes were reported to be down-regulated in the peripheral blood lymphocytes of multiple sclerosis patients in Israel (Achiron et al. (2004) *Ann Neurol*, 55, 410-417), and 15 of these genes were down-regulated in the T cells of Japanese multiple sclerosis patients (Satoh et al. (2006) *J Neuroimmunol*, 174, 108-118). The products of these genes included cytokines, chemokines and their receptors, signaling molecules and transcription factors (Table 1). Many of the genes down-regulated by cefuroxime and upregulated by ampicillin were reported to participate in Th2 and Treg pathways, and only a minority have been implicated in the Th1 pathway. It should be noted that the cytokine gene TNFα, considered to be pro-inflammatory, was found to have anti-inflammatory effects in knockout mice (Liu et al. (1998) *Nat Med*, 4, 78-83). The down-regulation of molecules in the Th2/Treg pathways by cefuroxime is consistent with its augmentation of EAE (Garren et al. (2001) *Immunity*, 15, 15-22) and AA (Mimran et al. (2004) *J Clin Invest*, 113, 924-932); in contrast, the up-regulation of these genes by ampicillin is consistent with its down-regulation of NOD diabetes (Elias et al. (1997) *Diabetes*, 46, 758-764). To verify the results detected by the gene array study, a panel of six genes was designed and tested by real-time PCR: CCR4, ACVR2, JAK1, STAT4, TLR2 and NFKBIE. The cDNA that was used was prepared from the same RNA used for the gene array experiment. The real-time PCR showed that each of the six genes that were downregulated in the gene-array experiment by cefuroxime treatment were suppressed by cefuroxime treatment in the RT-PCR experiment.

TABLE 1

Effects of cefuroxime and ampicillin on gene expression by CD4+ human T cells

| Gene | Full name/ Description | Reported to be decreased in MS patients | % decrease[1] by Cef | % increase by Amp | Function[2] | Th1/Th2[3] |
|---|---|---|---|---|---|---|
| Chemokines, cytokines and their receptors | | | | | | |
| CCR4 | Chemokine receptor 4 | Satoh et al. 2006 CCR5 | 39 ± 2 | +31 | Chemokine receptor | Expressed on Th2 cells and on diabetogenic Th1 cells |
| CCR6 | Chemokine receptor 6 | | 53 ± 5.6 | +83 | Chemokine receptor | Expressed on T-regulatory |
| CCR7 | Chemokine receptor 7 | Satoh et al. 2006 CCR5 | 38 ± 8.1 | +43 | Binds CCL21 | Expressed in EAE |
| CCL5 | Chemokine ligand 5 | | 21 ± 5.6 | +25 | Chemo-attractant for monocytes, memory T cells, eosinophils | Expressed in EAE lesion |
| CXCL10 | Chemokine 10 | | 39 ± 3 | +25 | CXCR3- the receptor Attracts Th1 cells | Antibody to CXCL10 exacerbates EAE Antibody to CXCL10 protects from EAE, DM |
| LTA | Lympho-toxin alpha | | 17 ± 10 | +48.5 | Cytokine | Blocking of LTA exacerbates Arthritis, Th1 |
| TNFα | Tumor necrosis factor alpha | Achiron et al. 2004 | 29 ± 8.5 | +39 | Cytokine | Th1, k/o mice show severe EAE |
| CCL11 | Chemokine ligand 11 | | 18 ± 6.6 | +107 | Cytokine Eotaxin, binds CCR3 | Th2, attracts eosinophils |
| SDF2 | Stromal cell derived factor 2 | | 28 ± 12 | +71 | Secreted | unknown |
| IL16 | Interleukin 16 | Satoh et al. 2006 | 50 ± 7.8 | +14 A low expression | Lymphocyte chemo-attractant factor | Th2 |
| IL1B | Interleukin-1 beta | Achiron et al. 2004 | 54 ± 7.0 | +64 A low expression | Cytokine | Pro-inflammatory |
| IL9R | Interleukin 9 receptor | | 27.5 ± 3 | No change | receptor | Th2 |

TABLE 1-continued

Effects of cefuroxime and ampicillin on gene expression by CD4+ human T cells

| Gene | Full name/ Description | Reported to be decreased in MS patients | % decrease[1] by Cef | % increase by Amp | Function[2] | Th1/Th2[3] |
|---|---|---|---|---|---|---|
| TNFRSF11 | Tumor necrosis factor receptor superfamily, member 11a | Achiron et al. 2004 Satoh et al. 2006 | 43 ± 2 | +81 A low expression | Membranal Activator of NFKB | unknown |
| IL2RB | Interleukin-2 receptor subunit beta | Satoh et al. 2006 | 50 ± 9.9 | +93 | Surface Binds IL2 | |
| IL2RG | Interleukin-2 receptor gamma | Satoh et al. 2006 | 57 ± 9.8 | +78 A low expression | Receptor | unknown |
| Surface receptors | | | | | | |
| TLR2 | Toll-like receptor 2 | | 52 ± 14 | +419 A low expression | Receptor | EAE Expression in Treg |
| CD28 | Cluster of differentiation 28 | | 51 ± 2.1 | +175 | Surface Binds B7-1 | Th2 |
| SELL | Selectin L | Satoh et al. 2006 | 46 ± 7.0 | +124 | Adhesion to high endothelial venules (HEV) | Th1 (unknown) |
| TGFβ related | | | | | | |
| ACVR2 | Activin receptor II | | 60 ± 14.8 | +85 A low expression | Activin is TGFbeta like | |
| ACVR1 | Activin receptor I | | 42 ± 0.7 | +53 A low expression | Activin is TGFbeta like | |
| TGIF | Transforming growth-interacting factor | | 43 ± 3.5 | +72 A low expression | Transcription factor represses SMAD2,3 | Anti Th2 |
| TGFBR3 | Transforming growth factor beta receptor III | Satoh et al. 2006 TGFBR1,2 | 44 ± 3.5 | +139 | Receptor | Regulatory |
| SMAD7 | | | 47 ± 4.2 | +34 A low expression | Inhibits TGFb | |
| SMAD4 | | Satoh et al. 2006 | 47 ± 7.0 | +85 | TGFb signal transduction pathways | Th3 |
| Kinases, signal transduction | | | | | | |
| MAP3K2 | Mitogen-activated protein 3kinase 2 | | 36 ± 12 | +93 | Regulates JNK ERK5 | unknown |
| MAP3K7 | Mitogen-activated protein 3kinase 7 | Satoh et al. 2006 | 46 ± 9.9 | +124 | TGFb signaling NfKB activation p38 MAPK | unknown |
| MAP3K1 | Mitogen-activated protein 3kinase 1 | Achiron et al. 2004 | 53 ± 12 | +63 A low expression | Activates ERK JNK | unknown |
| MAP2K4 | Mitogen-activated protein 2kinase 4 | Satoh et al. 2006 MAP2K1 | 52 ± 14.1 | +150 | | Th1 (unknown) |
| MAPK9 | Mitogen-activated protein kinase 9 | Achiron et al. 2004 | 42 ± 10.9 | +46 | JNK2 | Th1 (unknown) –/–No effect on EAE |

TABLE 1-continued

Effects of cefuroxime and ampicillin on gene expression by CD4+ human T cells

| Gene | Full name/ Description | Reported to be decreased in MS patients | % decrease[1] by Cef | % increase by Amp | Function[2] | Th1/Th2[3] |
|---|---|---|---|---|---|---|
| PAK1 | Protein kinase 1 | Satoh et al. 2006 PAK2 | 40 ± 2.4 | +111 | JNK Apoptosis | unknown |
| IRAK1 | Interleukin-1 receptor-associated kinase 1 | | 44 ± 2.1 | +171 | | Th1 IL10 |
| JAK1 | Janus kinase 1 | Satoh et al. 2006 | 53 ± 13.4 | +161 | Interferon α βγ transduction | Th1 and IL4 |
| Transcription factors | | | | | | |
| NFKB1 | Nuclear factor kappa-B 1 | Achiron et al. 2004 | 43 ± 3.5 | +31 | Transcription factor | Inhibits NFKB Th2 |
| NFKB2 | Nuclear factor kappa-B 2 | Achiron et al. 2004 Satoh et al. 2006 increased | 53 ± 10.6 | +195 | Transcription factor Lymphoma | unknown |
| NFKBIL1 | Nuclear factor-kappa-B inhibitor-like protein 1 | | 54 ± 12.5 | +191 | Transcription factor | unknown |
| NFKBIE | Nuclear factor of kappa light polypeptide gene enhancer in B-cells inhibitor, epsilon | Satoh et al. 2006 increased | 63 ± 11 | +132 | Inhibits NfkB | Th2 |
| SRF | Serum response factor | | 38 ± 1.9 | +58 | Transcription factor | unknown |
| EGR3 | Early growth response 3 | | 38 ± 2.8 | −25 | Transcription factor | Mitogenic activation induced in T cells, FAS-L expression |
| JUN | | Satoh et al. 2006 | 49 ± 2.2 | +65 | Interacts with c-fos to form a dimer. Interacts with smad3/smad4 heterodimer | Th2 (unknown) |
| RFXAP | Regulatory factor X-associated protein | | 27 ± 12 | +131 | MHCII expression | unknown |
| CREB1 | Cyclic AMP responsive element binding protein 1 | Satoh et al. 2006 | 19 ± 4.9 | +101 | Transcription factor | unknown |
| YY1 | Yin yang 1 | | 23 ± 9.1 | +152 | Transcription factor | Th2 activates IL4 |
| REL | | | 45 ± 1.9 | +132 | Transcription factor | Th1 IL12 |
| TRAF6 | TNF receptor associated factor 6 | Achiron et al. 2004 | 43 ± 3.5 | +39 A low expression | NfkB and JNK activation | Limit Th2 |
| TRAF5 | | | 43 ± 2.2 | +47 A low expression | | Limit Th2 |
| STAT1 | Signal transducer | Satoh et al. 2006 | 32 ± 11 | +85 | Transcription factor | Reg T Th1 |

TABLE 1-continued

Effects of cefuroxime and ampicillin on gene expression by CD4+ human T cells

| Gene | Full name/ Description | Reported to be decreased in MS patients | % decrease[1] by Cef | % increase by Amp | Function[2] | Th1/Th2[3] |
|---|---|---|---|---|---|---|
| | and activator of transcription 1 | | | | | |
| RFX5 | Regulatory factor X, 5 | | 36 ± 4.2 | +137 | MHCII expression | |
| STAT4 | Signal transducer and activator of transcription 4 | | 47 ± 9.3 | +11 | Transcription factor | Th1 Th2 |
| SP3 | | | 39 ± 9.9 | +47 | Transcription factor IL10 control | Th2 (unknown) |
| STAT6 | Signal transducer and activator of transcription 6 | | 47 ± 7.9 | no change | Transcription factor | Th2 IL4 |
| GFI1 | Growth factor independ1 | | 45 ± 14 | +10 | Transcription factor | Anti inflammatory |
| | | | Others | | | |
| CD40LG | CD40 ligand | | 33 ± 7.1 | +67 | Surface B cell interaction | Required for EAU autoimmune disease |
| RANBP5 | Importin beta3 | | 33 ± 3.5 | +108 | Nuclear proteins transport | unknown |
| ACTB | Actin beta | | 49 ± 11 | +196 | | |
| HRAS | | Satoh et al. 2006 | 30 ± 9.8 | −12 A low expression | Oncogene | unknown |
| CREBBP | CREB-binding protein | | 40 ± 9.9 | +49 | Acetylates nuclear proteins | |
| PIN1 | Peptidyl-prolyl cis-trans isomerase NIMA-interacting 1 | | 45 ± 12.1 | +105 | Isomerase | unknown |

[1]Percent decrease ±Standard deviation in cefuroxime treated human CD4 T cells relative to control
[2]Cellular function of the gene as found in databases
[3]Based on articles linking suggested gene to Th1, Th2 or Treg pathways. Data on some genes supported evidence linking the gene to more than one pathway (for example: CCR4, CXCL10).
"unknown" indicates unknown function in Th1/2 polarization.

Example 4

A Human T-Cell Protein of 67 kDa Specifically Binds Penicillin Covalently

Figure 2A:
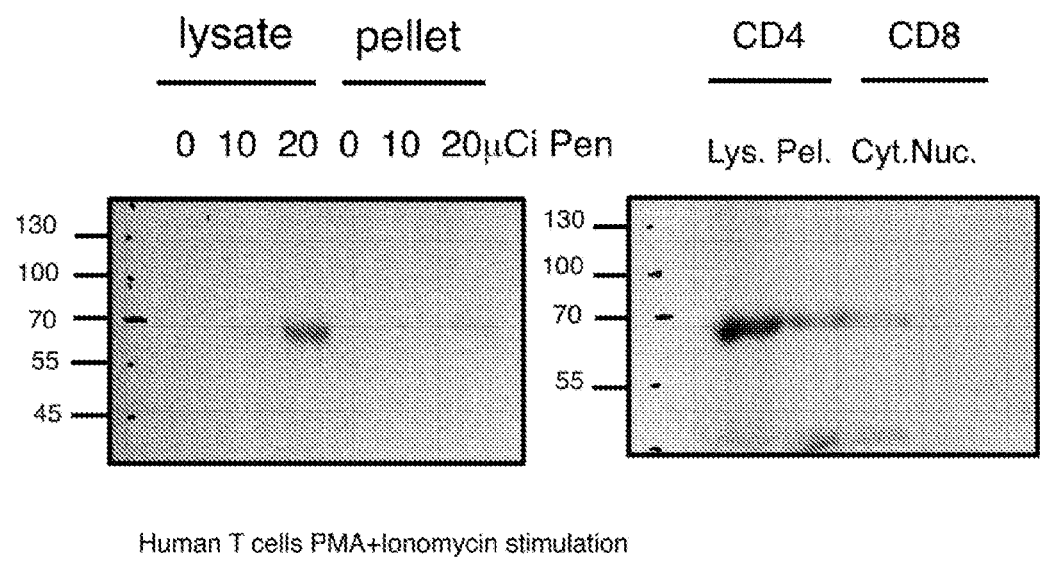
FIG. 2. A) Radioactively labeled penicillin binds to a 67 kDa band in human T-cell lysates. Left panel: CD4 T cells, right panel CD4 and CD8 T cells. Lys. signifies total lysate; Pel. pellet of total lysate; Cyt. Cytoplasmic; and Nuc. nuclear fraction. B) Results of the mass spectrometry report on the 67 kDa band.

Penicillin and other beta-lactam antibiotics have been shown to inhibit bacterial cell-wall synthesis by binding covalently to specific penicillin-binding proteins and thus interfere with their enzymatic activity. To test whether beta-lactam antibiotics might affect T-cell behavior likewise by covalently binding a key T-cell protein, purified CD4 or CD8 human T cells were incubated with 10 and 20 µCi of tritium-labeled lactam benzylpenicillin (Amersham, Buckinghamshire, UK) for 3 days during stimulation with PMA and Ionomycin. The stimulated T cells were collected, washed, lysed and their proteins were subjected to SDS-PAGE separation. Dried gels were exposed in intensifying screens to Xray film for 2 weeks at −80° C. As can be seen in FIG. 2A, a single major penicillin-protein radioactive band was detected at 67 kD in lysates of both CD4 and CD8 T cells. The intensity of the band was stronger at the 20 µCi concentration of penicillin.

Example 5

Identification of the 67 kD Penicillin-Binding Band as Albumin

The 67 kD lactam-binding band was isolated by activating human T cells in the presence of biotinylated ampicillin or biotinylated ceftriaxone. The cells were lysed and the lysates were purified by binding to a CAPTAVIDIN™ column (Invitrogen, Carlsbad, Calif. USA). The fractions binding the beta-lactam antibiotics were eluted by applying carbonate-bicarbonate buffer or by free biotin. The isolated protein band was subjected to enzymatic digestion and the resulting peptides were identified by mass spectrometry. The 67 kD protein from human CD4 T cells was identified as human serum albumin. Thus albumin seems to be a lactam-binding protein in human T cells.

Figure 3A:
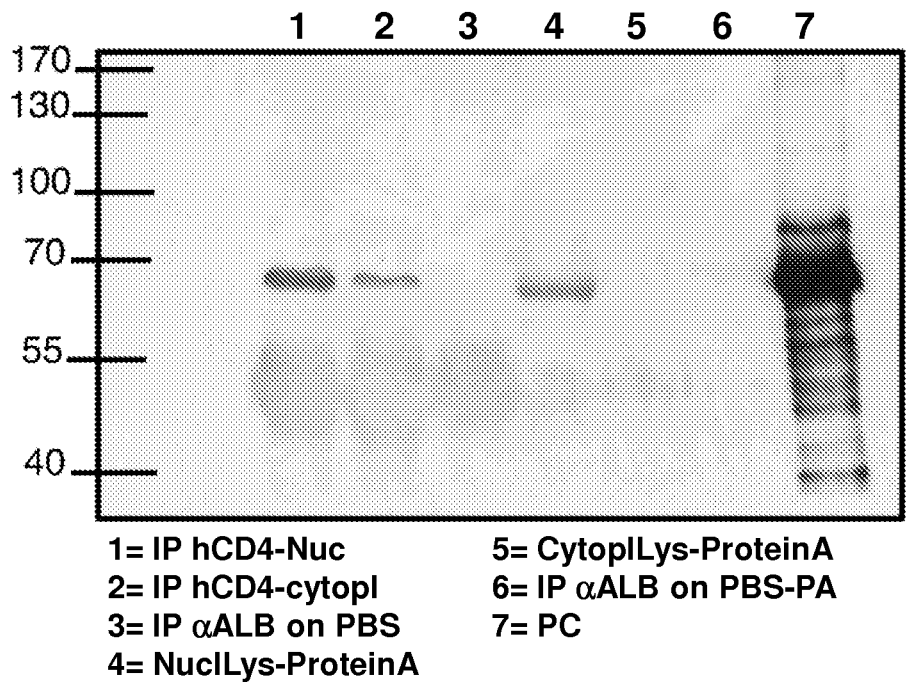
FIG. 3. A) Immunoprecipitation of 67 kDa band molecule by an anti-human serum albumin antibody. B) T cells express albumin modifiable by penicillin. The Pen 9-labelled 67 kD band is present only in penicillin-treated T cells. Abbreviation: Pen—penicillin, Amp—ampicillin, Zin—zinacef-cefuroxime, Chlor—chloramphenicol, Vanc—vancomycin.

As albumin is a known contaminant in sequencing studies, the isolation of the 67 kD band from penicillin-treated cells was repeated using immuno-precipitation (IP) with anti-human serum albumin (anti-HSA, αALB). Cytoplasmic or nuclear lysates of human CD4 T cells treated with penicillin were incubated with rabbit polyclonal anti-human albumin (Sigma), precipitated with protein A sepharose and run in an SDS gel. Lysates without the protein A-bound complex (collected after the immunoprecipitation) were run as controls. Western blotting was then performed with an antibody that binds specifically to penicillin bound to proteins—pen 9 (de Haan et al. (1985) Int Arch Allergy Appl Immunol, 76, 42-46). FIG. 3A shows the results of this experiment. The 67 kD band appears in the IP of cytoplasmic ("IP hCD4-cytopl") and nuclear fractions ("IP hCD4-Nuc"); the band is absent from a lysate of the cytoplasmic fraction collected after the immunoprecipitation ("CytoplLys-ProteinA", lane 5). In other words, IP with anti-HSA antibody resulted in the disappearance of the penicillin-protein band from the cytoplasmic lysate, suggesting that except for albumin there are no other proteins of a similar molecular weight that are modified by penicillin.

Example 6

Analysis of T-Cell Beta-Lactam Binding by Anti-Penicilloyl-Albumin Antibody

Figure 3B:
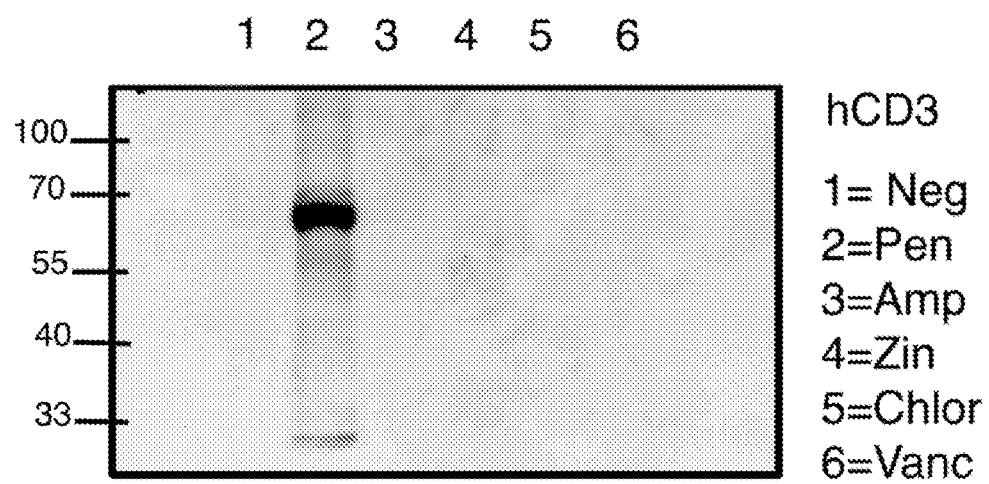

A monoclonal anti-penicilloyl-albumin antibody was used to further confirm that the beta-lactam binding molecule produced by human T cells is albumin. When penicillin binds covalently to a protein, the beta-lactam ring binds to a lysine residue. A monoclonal antibody called Pen 9 is specific to the thiazolidine ring of penicillin bound to albumin (de Haan et al. (1985), as above). To test the reactivity of Pen 9 in the present system, purified human T cells were activated by mitogenic treatment in the presence of the beta-lactam antibiotics penicillin and ampicillin or with other families of antibiotics in culture, and the lysates were tested by western blot with Pen 9. FIG. 3B shows that the Pen 9 reacted specifically to a major protein of the penicillin-treated T cells and not to any other antibiotic in human CD3 T cells. It should be noted that Pen 9 did not bind to the ampicillin-treated T cells; apparently the albumin molecule modified by ampicillin does not present the specific epitope presented by the penicillin-albumin molecule.

Example 7

Pen 9 Monoclonal Antibody Detects Penicillin-Albumin In Vivo

Figure 4A:
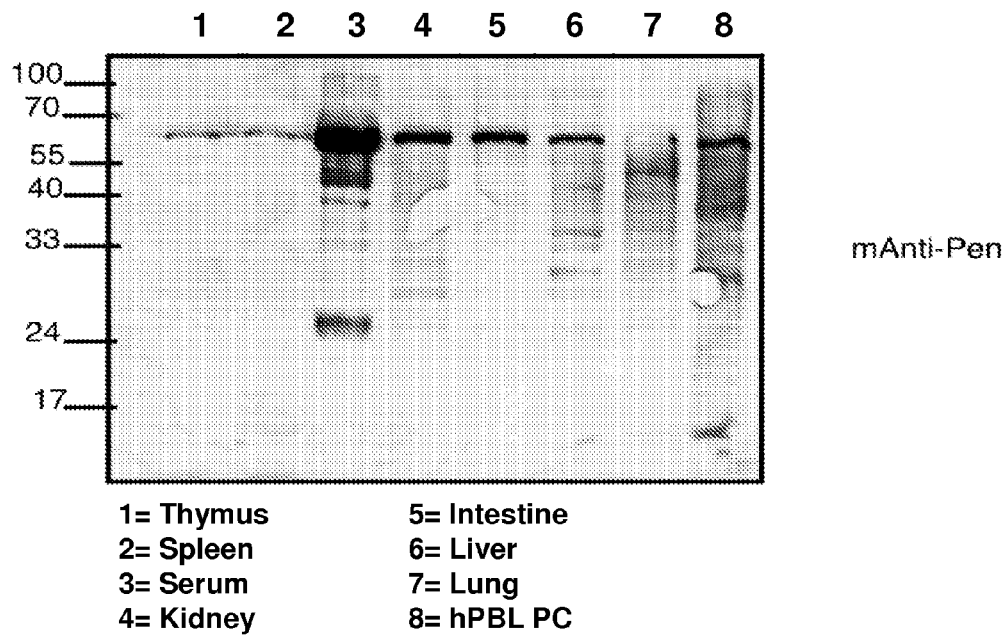
FIG. 4. A) Detection of in vivo penicillin-labeled proteins. The 67 kD band is present in all tissues and is most abundant in serum sample. B) Western blot analysis of various cell lines treated with penicillin shows the dominant 67 kDa band in most samples.
Figure 4B:
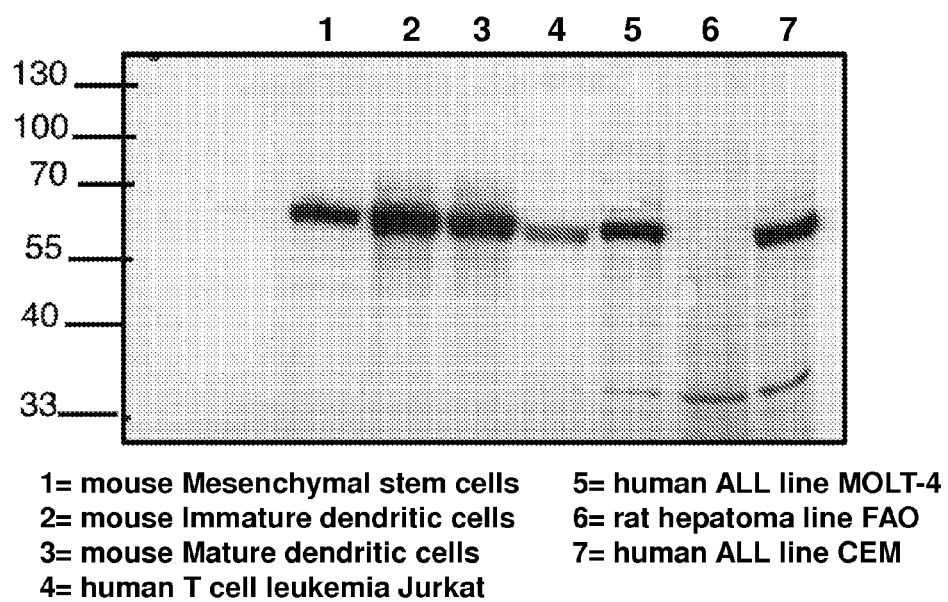

To learn whether penicillin binds albumin in vivo, Lewis rats were injected intraperitoneally with penicillin G (50 mg/rat) and 2 hours later various tissue lysates were tested for reactivity with pen 9 antibody in western blot. The results are shown in FIG. 4A. The 67 kD band representing penicilloylated albumin appears in all tissues examined and is most abundant in serum. Lysates of various cell lines raised in vitro were also tested. FIG. 4B shows that the penicillin-modified albumin band could be detected in mesenchymal stem cells, dendritic cells, Jurkat, MOLT4, FAO and CEM lines. Albumin was absent in the FAO rat hepatoma cell line that is known to have dedifferentiated and to have lost its expression of albumin (Cairo et al. Exp Cell Res, 206, 255-260).

Example 8

Albumin mRNA is Expressed by T Cells

Figure 5:
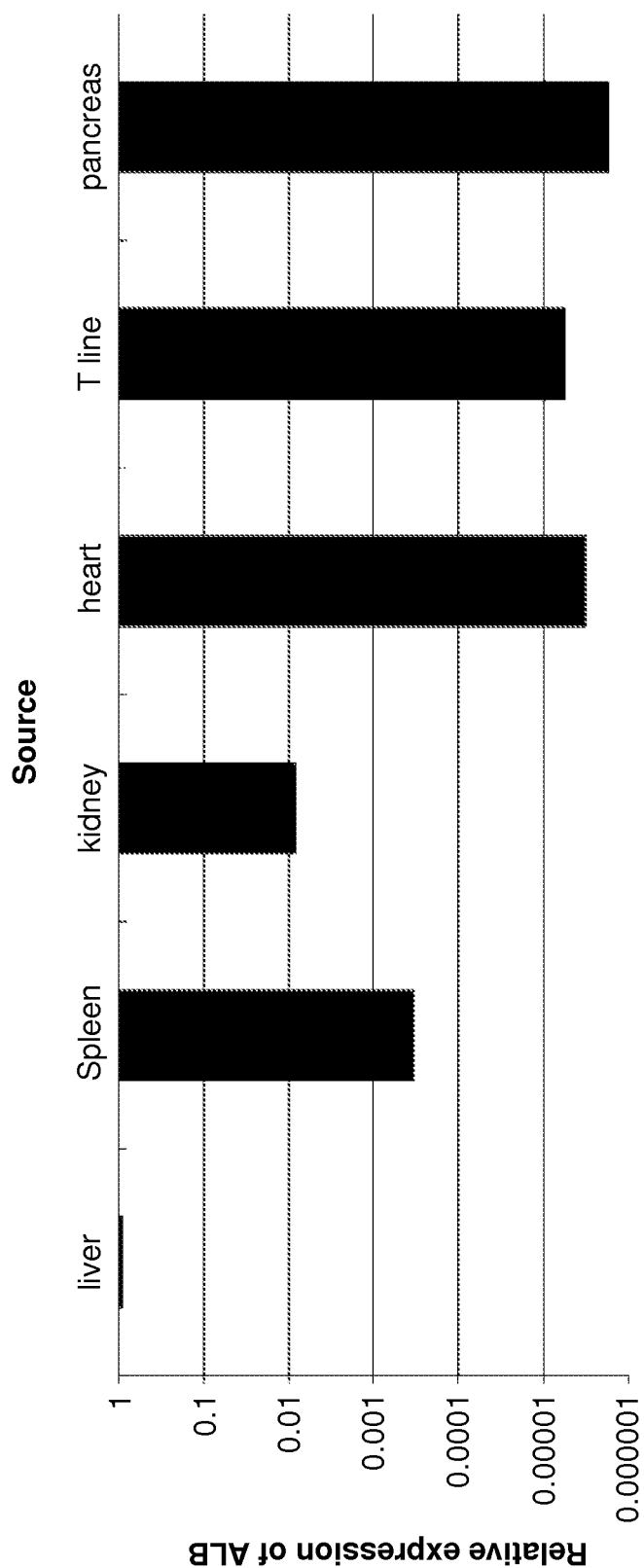
FIG. 5. Relative expression of albumin mRNA in various tissues by RT-PCR.

To test whether T cells might indeed produce albumin, the expression of albumin mRNA in rat T cells compared to other tissues was analyzed by RT-PCR. Total RNA was extracted from various tissues and cDNA was prepared. RT-PCR was performed and the quantities relative to liver were depicted. FIG. 5 shows that albumin mRNA could be detected in rat T cells, as well as in spleen, kidney, heart and pancreas. A similar level of expression was detected in human CD4 T cells.

Example 9

Penicillin-Modified Albumin is Taken Up by T Cells

Figure 6A:
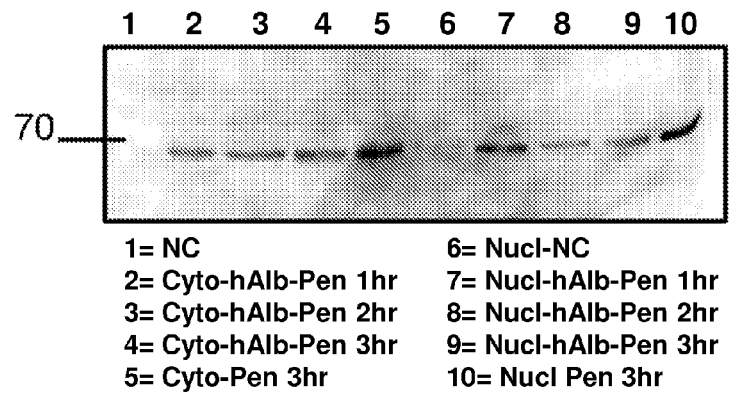
FIG. 6. A) Western blot of human CD4 T cells incubated with Penicillin-modified albumin. B) Penicillin-modified albumin augments the pathogenicity of BP10 line.

To test whether penicillin-modified albumin can enter T cells, human serum albumin was incubated with penicillin, and then dialysed extensively. The resulting penicillin-modified-albumin was incubated with purified human CD4 T cells for 3 hours, and the cells were lysed and tested by western blot with monoclonal Pen 9 antibody. T cells were harvested after 1, 2, or 3 hrs. Cytoplasmic ("Cyto") and nuclear ("Nucl") fractions were run on SDS transferred to nitrocellulose and tested with Pen 9 antibody. FIG. 6A shows the results. The penicillin-modified albumin ("hAlb") detected by Pen 9 entered the cells and was detectable in the nuclei within 1 hr. Cytoplasmic and nuclear penicillin-labeled-albumin was seen after 1 hr, and peaked at 3 hr. In additional experiments, it was found that nuclear entry of the penicillin-modified albumin was augmented upon T cell activation for 1 hr with PMA and Ionomycin. Thus, T cells, both in the resting and activated states, can take up penicillin-modified albumin and transport it to the nucleus.

Example 10

Penicillin-Modified Albumin Augments the Pathogenicity of the BP10 Line

Figure 6B:
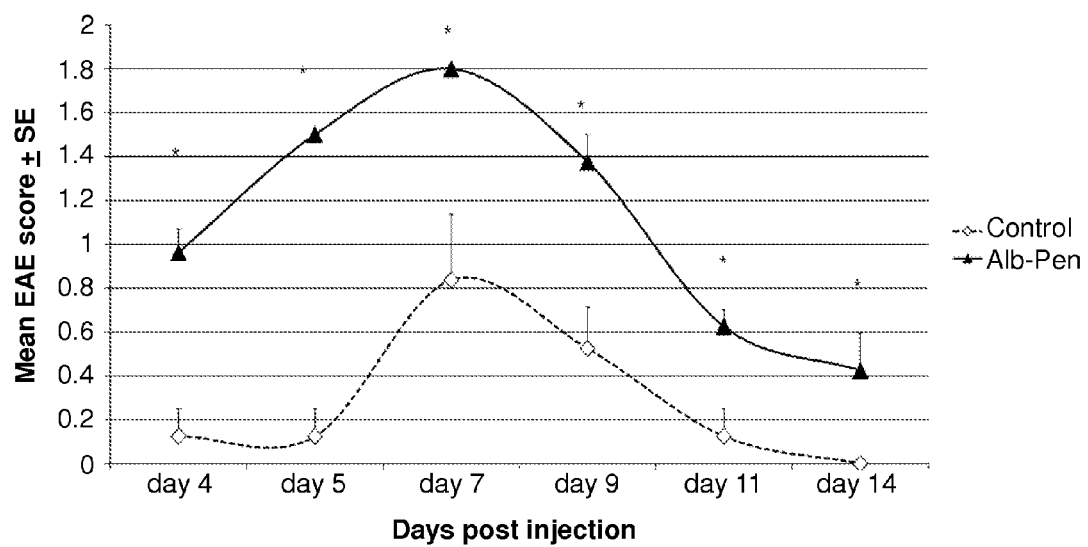

To test whether the penicillin-modified albumin moiety itself could enhance the effector functions of a T-cell line, the encephalitogenic BP 10 line was stimulated with penicillin-modified albumin (at 5 mg/ml) for 3 days in stimulation medium and tested in vivo the capacity of the line to mediate EAE (human albumin was incubated or not with penicillin (100 mg/ml for 2 hrs at 37° C.), dialysed against PBS, and then added at 5 mg/ml to stimulation medium of BP10 line). A control group was injected with the untreated line. FIG. 6B shows that similar to penicillin alone, penicillin-modified albumin enhanced the pathogenicity of the T cells. Penicillin-modified rat albumin ("Alb-Pen") could also enhance the encephalogenicity of the BP10 line. In additional experiments, unmodified human albumin alone had no significant effect on the severity of the EAE mediated by the line.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating type I diabetes in a subject in need thereof, the method comprising administering to the subject a pharmaceutical composition comprising ampicillin or a salt thereof, thereby treating type I diabetes in said subject.

2. The method of claim 1, wherein the administered pharmaceutical composition comprises a sub-antibacterial dose of ampicillin.

3. The method of claim 1, wherein the pharmaceutical composition comprising ampicillin is administered in a sub-antibacterial treatment regime.

4. The method of claim 1, wherein the ampicillin is conjugated to a protein, and wherein the ampicillin-protein conjugate is devoid of antibacterial activity.

5. The method of claim 4, wherein the ampicillin is conjugated to albumin.

6. The method of claim 5, wherein the albumin is human serum albumin.

7. The method of claim 1, wherein the subject is human.

8. The method of claim 1, wherein the subject is a non-human mammal.

9. The method of claim 1, wherein the subject is newly diagnosed with type I diabetes.

10. The method of claim 1, wherein the subject is at risk of developing type I diabetes.

* * * * *

```
                            SEQUENCE LISTING

<160> NUMBER OF SEQ ID NOS: 18

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
cccgattact ccgtgt                                                         16

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
tggcgttttg gaatccata                                                      19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
atgcgctatt agttcgttac                                                     20

<210> SEQ ID NO 4
<211> LENGTH: 16
<212> TYPE: DNA
<213> ORGANISM: Artificial Sequence
<220> FEATURE:
<223> OTHER INFORMATION: Primer

<400> SEQUENCE: 4
catggtcgcc tgttca                                                         16

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
tagctctagg agggctg                                                        17

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
```

-continued accacaacca tgcctta                                                  17

<210> SEQ ID NO 7
<211> LENGTH: 16
<212> TYPE: DNA
<213> ORGANISM: Artificial Sequence
<220> FEATURE:
<223> OTHER INFORMATION: Primer

<400> SEQUENCE: 7
atctccgcgt aaggaa                                                   16

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
tgggactaac aatcgtg                                                  17

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
tcctagagac cctggtg                                                  17

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
ggactgcgtg taagatg                                                  17

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
aggagtatta caccgtcaag                                               20

<210> SEQ ID NO 12
<211> LENGTH: 16
<212> TYPE: DNA
<213> ORGANISM: Artificial Sequence
<220> FEATURE:
<223> OTHER INFORMATION: Primer

<400> SEQUENCE: 12
gggttgggcc tatcat                                                   16

<210> SEQ ID NO 13
<211> LENGTH: 17
<212> TYPE: DNA
<213> ORGANISM: Artificial Sequence

```
<220> FEATURE:
<223> OTHER INFORMATION: Primer

<400> SEQUENCE: 13
acatcctgcg agactac                                                  17

<210> SEQ ID NO 14
<211> LENGTH: 16
<212> TYPE: DNA
<213> ORGANISM: Artificial Sequence
<220> FEATURE:
<223> OTHER INFORMATION: Primer

<400> SEQUENCE: 14
caccgcatac acactt                                                   16

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
cttctggagc ccattg                                                   16

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
acggtacatc cacgtag                                                  17

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
gactttgtgg tagaggca                                                 18

<210> SEQ ID NO 18
<211> LENGTH: 16
<212> TYPE: DNA
<213> ORGANISM: Artificial Sequence
<220> FEATURE:
<223> OTHER INFORMATION: Primer

<400> SEQUENCE: 18
aaaacgtgga gtcagc                                                   16
```